(12) United States Patent
Ouyang et al.

(10) Patent No.: US 11,844,498 B2
(45) Date of Patent: *Dec. 19, 2023

(54) HANDHELD SURGICAL ENDOSCOPE

(71) Applicant: UroViu Corp., Bellevue, WA (US)

(72) Inventors: Xiaolong Ouyang, Bellevue, WA (US);
Shih-Ping Wang, Los Altos, CA (US);
Robert K. Deckman, San Bruno, CA (US)

(73) Assignee: UroViu Corporation, Bellevue, WA (US)

( * ) Notice: Subject to any disclaimer, the term of this patent is extended or adjusted under 35 U.S.C. 154(b) by 62 days.

This patent is subject to a terminal disclaimer.

(21) Appl. No.: 17/122,282

(22) Filed: Dec. 15, 2020

(65) Prior Publication Data

US 2021/0093169 A1    Apr. 1, 2021

Related U.S. Application Data

(60) Division of application No. 16/413,160, filed on May 15, 2019, now Pat. No. 10,869,592, which is a
(Continued)

(51) Int. Cl.
*A61B 1/00* (2006.01)
*A61B 1/06* (2006.01)
*A61B 1/018* (2006.01)

(52) U.S. Cl.
CPC ...... *A61B 1/00144* (2013.01); *A61B 1/00034* (2013.01); *A61B 1/00048* (2013.01);
(Continued)

(58) Field of Classification Search
None
See application file for complete search history.

(56) References Cited

U.S. PATENT DOCUMENTS 4,854,302 A    8/1989  Allred, III
4,979,497 A    12/1990 Matsura
(Continued)

FOREIGN PATENT DOCUMENTS

CN    102858275    1/2013
CN    105636621    6/2016
(Continued)

OTHER PUBLICATIONS

International Search Report and Written Opinion of PCT/US2016/18670, dated Jul. 12, 2016.
(Continued)

*Primary Examiner* — John P Leubecker
(74) *Attorney, Agent, or Firm* — Wissing Miller LLP

(57) ABSTRACT

A handheld surgical endoscope has a disposable, single-use handle, cannula and an imaging module at a distal tip. A multiple-use display unit is removably mounted on and supported by the handle and includes a touch-sensitive display screen configured to respond to touch commands to control taking of images with the imaging module and further configured to display the images. The display unit and the handle include respective mechanical connectors that engage each other to removably mount the display unit on the handle by sliding motion relative to each other, and the display unit is removable tool-free from said handle for disposal of the handle and cannula after a medical procedure therewith.

7 Claims, 27 Drawing Sheets

Related U.S. Application Data continuation-in-part of application No. 16/407,028, filed on May 8, 2019, now Pat. No. 11,253,141, which is a division of application No. 14/913,867, filed as application No. PCT/US2016/018670 on Feb. 19, 2016, now Pat. No. 10,874,287.

(60) Provisional application No. 62/119,521, filed on Feb. 23, 2015.

(52) U.S. Cl.
CPC ...... *A61B 1/00052* (2013.01); *A61B 1/00103* (2013.01); *A61B 1/018* (2013.01); *A61B 1/0676* (2013.01); *A61B 1/0684* (2013.01); *A61B 1/00016* (2013.01)

(56) References Cited

U.S. PATENT DOCUMENTS

| | | | |
|---|---|---|---|
| 5,010,876 A | 4/1991 | Henley | |
| 5,188,093 A | 2/1993 | Lafferty | |
| 5,237,984 A | 8/1993 | Williams, III | |
| 5,281,214 A | 1/1994 | Wilkins | |
| 5,323,767 A | 6/1994 | Lafferty | |
| 5,329,936 A | 7/1994 | Lafferty | |
| 5,474,057 A | 12/1995 | Makower | |
| 5,486,155 A | 1/1996 | Muller | |
| 5,527,332 A * | 6/1996 | Clement | A61B 10/0275 606/171 |
| 5,549,547 A | 8/1996 | Cohen | |
| 5,569,163 A | 10/1996 | Francis | |
| 5,578,030 A * | 11/1996 | Levin | A61B 18/082 606/49 |
| 5,666,561 A | 9/1997 | Stephenson | |
| 5,667,472 A | 9/1997 | Finn | |
| 5,667,476 A | 9/1997 | Frassica et al. | |
| 5,785,644 A | 7/1998 | Grabover | |
| 5,860,953 A | 1/1999 | Snoke | |
| 5,873,814 A | 2/1999 | Adair | |
| 5,895,361 A | 4/1999 | Turturro | |
| 5,928,137 A | 7/1999 | Green | |
| 5,935,141 A | 8/1999 | Weldon | |
| 5,957,947 A | 9/1999 | Wattiez | |
| 6,007,531 A | 12/1999 | Snoke | |
| 6,007,546 A | 12/1999 | Snow | |
| 6,017,322 A | 1/2000 | Snoke | |
| 6,033,378 A | 3/2000 | Lundquist | |
| 6,059,719 A | 5/2000 | Yamamato et al. | |
| 6,095,970 A | 8/2000 | Hidaka | |
| 6,174,307 B1 | 1/2001 | Daniel | |
| 6,210,416 B1 | 4/2001 | Chu | |
| 6,211,904 B1 | 4/2001 | Adair | |
| 6,221,007 B1 | 4/2001 | Green | |
| 6,221,070 B1 | 4/2001 | Tu et al. | |
| 6,261,226 B1 | 7/2001 | McKenna | |
| 6,280,386 B1 | 8/2001 | Alfano | |
| 6,331,174 B1 | 12/2001 | Reinhard | |
| 6,387,043 B1 | 5/2002 | Yoon | |
| 6,398,743 B1 | 6/2002 | Halseth | |
| 6,507,699 B2 | 1/2003 | Lemoine | |
| 6,518,823 B1 | 2/2003 | Kawai | |
| 6,673,087 B1 | 1/2004 | Chang | |
| 6,793,882 B1 | 9/2004 | Verschuur | |
| 6,917,380 B1 | 7/2005 | Tay | |
| 7,256,446 B2 | 8/2007 | Hu | |
| 7,428,378 B1 | 9/2008 | Warpakowski | |
| 7,507,205 B2 | 3/2009 | Borovsky | |
| 7,591,799 B2 | 9/2009 | Selkee | |
| 7,606,609 B2 | 10/2009 | Muranushi | |
| 7,780,650 B2 | 8/2010 | Frassica | |
| 7,798,995 B2 | 9/2010 | Yue | |
| 7,931,616 B2 | 4/2011 | Selkee | |
| 7,946,981 B1 | 5/2011 | Cubb | |
| 8,057,464 B2 | 9/2011 | Chen | |
| 8,052,609 B2 | 11/2011 | Harhen | |
| 8,187,171 B2 | 5/2012 | Irion | |
| 8,197,398 B2 | 6/2012 | Scholly | |
| 8,235,975 B2 | 8/2012 | Chen | |
| 8,361,775 B2 | 4/2013 | Flower | |
| 8,460,182 B2 | 6/2013 | Ouyang | |
| 8,523,808 B2 | 9/2013 | Selkee | |
| 8,696,552 B2 | 4/2014 | Whitman | |
| 8,803,960 B2 | 8/2014 | Sonnenschein | |
| 8,834,357 B2 | 9/2014 | Oskin | |
| 8,845,522 B2 | 9/2014 | McIntyre | |
| 8,952,312 B2 | 2/2015 | Blanqart | |
| 8,998,844 B2 | 4/2015 | Reed | |
| 9,649,014 B2 | 5/2017 | Ouyang | |
| 9,736,342 B2 | 8/2017 | Mueckl | |
| 9,895,048 B2 | 2/2018 | Ouyang | |
| 10,278,563 B2 | 5/2019 | Ouyang | |
| 10,292,571 B2 | 5/2019 | Ouyang | |
| 10,595,710 B2 | 3/2020 | Gill | |
| 2001/0007051 A1 | 7/2001 | Nakashima | |
| 2001/0049509 A1 | 12/2001 | Sekine | |
| 2003/0016284 A1 | 1/2003 | Squilla | |
| 2003/0023142 A1 | 1/2003 | Grabover | |
| 2003/0078476 A1 | 4/2003 | Hill | |
| 2003/0078502 A1 | 4/2003 | Miyaki et al. | |
| 2003/0151680 A1 | 8/2003 | McDermott | |
| 2003/0199735 A1 | 10/2003 | Dickopp | |
| 2004/0054254 A1 | 3/2004 | Miyake | |
| 2004/0054259 A1 | 3/2004 | Hasegawa | |
| 2004/0138558 A1 | 7/2004 | Dunki-Jacobs | |
| 2004/0162572 A1 | 8/2004 | Sauer | |
| 2005/0010178 A1 | 1/2005 | Katz | |
| 2005/0264687 A1 | 1/2005 | Murayama | |
| 2005/0049459 A1 | 3/2005 | Hern | |
| 2005/0065397 A1 | 3/2005 | Saadat | |
| 2005/0085695 A1 | 4/2005 | Sherner | |
| 2005/0154262 A1 | 7/2005 | Banik | |
| 2005/0159646 A1 | 7/2005 | Nordstrom | |
| 2005/0177027 A1 | 8/2005 | Hirata | |
| 2005/0277874 A1 | 12/2005 | Selkee | |
| 2005/0277875 A1 | 12/2005 | Selkee | |
| 2006/0052710 A1 | 3/2006 | Miura | |
| 2006/0063976 A1 | 3/2006 | Aizenfeld | |
| 2006/0114986 A1 | 6/2006 | Knapp | |
| 2006/0152601 A1 | 7/2006 | Parekh | |
| 2006/0167340 A1 | 7/2006 | Peas | |
| 2006/0171693 A1 | 8/2006 | Todd | |
| 2006/0173245 A1 | 8/2006 | Todd | |
| 2006/0184227 A1 | 8/2006 | Rust | |
| 2006/0259124 A1 | 11/2006 | Matsuoka | |
| 2006/0287576 A1 | 12/2006 | Tsuji | |
| 2007/0060789 A1 | 3/2007 | Uchimura | |
| 2007/0081920 A1 | 4/2007 | Murphy | |
| 2007/0117437 A1 | 5/2007 | Boehnlein | |
| 2007/0129604 A1 | 6/2007 | Hatcher | |
| 2007/0162095 A1 | 7/2007 | Kimmel | |
| 2007/0167678 A1 | 7/2007 | Moskowitz | |
| 2007/0167868 A1 | 7/2007 | Sauer | |
| 2007/0173693 A1 | 7/2007 | Refael | |
| 2007/0187875 A1 | 8/2007 | Terasaki | |
| 2007/0188604 A1 | 8/2007 | Miyamoto | |
| 2007/0197875 A1 | 8/2007 | Osaka | |
| 2007/0210162 A1 | 9/2007 | Keen | |
| 2007/0225556 A1 | 9/2007 | Ortiz | |
| 2007/0238927 A1 | 10/2007 | Ueno | |
| 2007/0249904 A1 | 10/2007 | Amano | |
| 2008/0004642 A1 | 1/2008 | Birk | |
| 2008/0071144 A1 | 3/2008 | Kimmel | |
| 2008/0097550 A1 | 4/2008 | Dicks | |
| 2008/0108869 A1 | 5/2008 | Sanders | |
| 2008/0195125 A1 | 8/2008 | Orbay | |
| 2008/0195128 A1 | 8/2008 | Orbay | |
| 2008/0225410 A1 | 9/2008 | Ning | |
| 2008/0234547 A1 | 9/2008 | Irion et al. | |
| 2008/0255416 A1 | 10/2008 | Gilboa | |
| 2008/0262306 A1 | 10/2008 | Kawai | |
| 2008/0300456 A1 | 12/2008 | Irion | |
| 2009/0027489 A1 | 1/2009 | Takemura | |
| 2009/0065565 A1 | 3/2009 | Lemoine | |

(56) References Cited

U.S. PATENT DOCUMENTS

| | | |
|---|---|---|
| 2009/0076321 A1 | 3/2009 | Suyama |
| 2009/0076328 A1 | 3/2009 | Root |
| 2009/0080214 A1 | 3/2009 | Watanabe |
| 2009/0105538 A1 | 4/2009 | Van Dam |
| 2009/0118580 A1 | 5/2009 | Sun |
| 2009/0118641 A1 | 5/2009 | Van Dam |
| 2009/0149713 A1 | 7/2009 | Niida |
| 2009/0225159 A1 | 9/2009 | Schneider |
| 2009/0227897 A1 | 9/2009 | Wendt |
| 2009/0286412 A1 | 11/2009 | Ikeda |
| 2009/0287663 A1 | 11/2009 | Takeuchi |
| 2010/0069834 A1 | 3/2010 | Schultz |
| 2010/0094216 A1 | 4/2010 | Yue |
| 2010/0095969 A1 | 4/2010 | Schwartz |
| 2010/0101569 A1 | 4/2010 | Kim |
| 2010/0121142 A1 | 5/2010 | Ouyang |
| 2010/0157039 A1 | 6/2010 | Sugai |
| 2010/0160914 A1 | 6/2010 | Bastian |
| 2010/0168827 A1 | 7/2010 | Schultz |
| 2010/0191051 A1 | 7/2010 | Miyake |
| 2010/0191053 A1 | 7/2010 | Garcia |
| 2010/0234736 A1 | 9/2010 | Corl |
| 2010/0026201 A1 | 10/2010 | Frangioni |
| 2011/0009694 A1 | 1/2011 | Schultz |
| 2011/0034769 A1 | 2/2011 | Adair |
| 2011/0037876 A1 | 2/2011 | Talbert |
| 2011/0554446 | 3/2011 | Schultz |
| 2011/0092775 A1 | 4/2011 | Deshmukh |
| 2011/0105839 A1 | 5/2011 | Hoffman |
| 2011/0112622 A1 | 5/2011 | Phan |
| 2011/0124961 A1 | 5/2011 | Zimmon |
| 2011/0130627 A1 | 6/2011 | McGrail |
| 2011/0211115 A1 | 9/2011 | Tsai |
| 2011/0213206 A1 | 9/2011 | Boutillette |
| 2011/0245602 A1 | 10/2011 | Brannon |
| 2011/0264191 A1 | 10/2011 | Rothstein |
| 2011/0288482 A1 | 11/2011 | Farrell |
| 2011/0313245 A1 | 12/2011 | Scholly |
| 2012/0016191 A1 | 1/2012 | Ito |
| 2012/0040305 A1 | 2/2012 | Karazivan |
| 2012/0041533 A1 | 2/2012 | Bertolino |
| 2012/0053515 A1 | 3/2012 | Crank |
| 2012/0100729 A1 | 4/2012 | Edidin |
| 2012/0165916 A1 | 6/2012 | Jordan |
| 2012/0178991 A1 | 7/2012 | Clark |
| 2012/0226103 A1 | 9/2012 | Gunday |
| 2012/0236138 A1 | 9/2012 | Liu |
| 2012/0245242 A1 | 9/2012 | Peiffer |
| 2012/0245418 A1 | 9/2012 | Boulais |
| 2012/0253116 A1 | 10/2012 | Sniffin |
| 2012/0259203 A1 | 10/2012 | Devereux |
| 2012/0286020 A1 | 11/2012 | Smith |
| 2012/0289858 A1 | 11/2012 | Ouyang |
| 2013/0006145 A1* | 1/2013 | Toomey ............... A61B 8/481 600/567 |
| 2013/0035553 A1 | 2/2013 | Kongstorum |
| 2013/0046142 A1 | 2/2013 | Remijan |
| 2013/0057667 A1 | 5/2013 | McGrath |
| 2013/0150672 A1 | 6/2013 | Fujitani |
| 2013/0172676 A1 | 7/2013 | Levy |
| 2013/0190561 A1 | 7/2013 | Oskin |
| 2013/0225921 A1 | 8/2013 | Liu |
| 2013/0253402 A1 | 9/2013 | Badawi |
| 2013/0096378 A1 | 10/2013 | Alexander |
| 2013/0289559 A1 | 10/2013 | Reid |
| 2013/0324973 A1 | 12/2013 | Reed |
| 2013/0345514 A1 | 12/2013 | Manion |
| 2014/0022649 A1 | 1/2014 | Echhardt |
| 2014/0107416 A1 | 4/2014 | Bimkrant |
| 2014/0111634 A1 | 4/2014 | Mueckl |
| 2014/0154399 A1 | 6/2014 | Weikart |
| 2014/0180007 A1 | 6/2014 | Edidin |
| 2014/0188211 A1 | 7/2014 | Roeder |
| 2014/0213848 A1 | 7/2014 | Moskowitz |
| 2014/0228635 A1 | 8/2014 | Tuliakov |
| 2014/0275763 A1 | 9/2014 | King |
| 2014/0296866 A1 | 10/2014 | Salman |
| 2014/0323991 A1 | 10/2014 | Tang |
| 2015/0005575 A1 | 1/2015 | Kobayashi |
| 2015/0011830 A1 | 1/2015 | Hunter |
| 2015/0018622 A1 | 1/2015 | Tesar |
| 2015/0018710 A1 | 1/2015 | Furlong |
| 2015/0150441 A1 | 6/2015 | Ouyang |
| 2015/0164313 A1 | 6/2015 | Oyuang |
| 2015/0196197 A1 | 7/2015 | Kienzle |
| 2015/0238175 A1* | 8/2015 | Seiger ............... A61B 10/0275 600/566 |
| 2015/0238251 A1 | 8/2015 | Shikhman |
| 2015/0297311 A1 | 10/2015 | Tesar |
| 2016/0073853 A1 | 3/2016 | Venkatesan et al. |
| 2016/0077008 A1 | 3/2016 | Takasu |
| 2016/0174819 A1 | 6/2016 | Ouyang |
| 2016/0334694 A1 | 11/2016 | Liu |
| 2016/0367119 A1 | 12/2016 | Ouyang |
| 2017/0086651 A1 | 3/2017 | Sato |
| 2017/0181853 A1 | 6/2017 | Rothstein |
| 2017/0188793 A1 | 7/2017 | Ouyang |
| 2017/0188795 A1 | 7/2017 | Ouyang |
| 2017/0215699 A1 | 8/2017 | Ouyang |
| 2017/0295347 A1 | 10/2017 | Schneider |
| 2017/0310858 A1 | 10/2017 | Mueckl |
| 2018/0132700 A1 | 5/2018 | Ouyang |
| 2018/0184892 A1 | 7/2018 | Truckai |
| 2018/0235441 A1 | 8/2018 | Huang |
| 2018/0256009 A1 | 9/2018 | Ouyang |
| 2018/0289241 A1 | 10/2018 | Zhou |
| 2019/0029497 A1 | 1/2019 | Mirza |
| 2019/0142262 A1 | 5/2019 | Inglis |
| 2019/0216325 A1 | 7/2019 | Ouyang |
| 2019/0223691 A1 | 7/2019 | Takatsuji |
| 2019/0246873 A1 | 8/2019 | Lu |
| 2019/0246884 A1 | 8/2019 | Lu et al. |
| 2019/0282071 A1 | 9/2019 | Ouyang |
| 2019/0282073 A1 | 9/2019 | Truckai |
| 2019/0320879 A1 | 10/2019 | Langell |
| 2019/0374095 A1 | 12/2019 | Lord |
| 2020/0204776 A1 | 6/2020 | Themelis |
| 2020/0214739 A1 | 7/2020 | Shi |
| 2020/0275827 A1 | 9/2020 | Weise |
| 2021/0052383 A1 | 2/2021 | Rothstein |
| 2021/0228806 A1 | 7/2021 | Streeter |
| 2021/0401277 A1 | 12/2021 | Ouyang |

FOREIGN PATENT DOCUMENTS

| | | |
|---|---|---|
| CN | 106132273 | 11/2016 |
| CN | 110234265 | 9/2019 |
| EP | 1690512 | 8/2006 |
| EP | 2560589 | 4/2010 |
| EP | 3384879 | 4/2011 |
| EP | 2749258 | 7/2014 |
| EP | 3078354 | 10/2016 |
| EP | 2721992 | 4/2018 |
| JP | 2009148420 | 7/2009 |
| WO | 2011133792 | 10/2011 |
| WO | 2012060932 | 5/2012 |
| WO | 2012151073 | 11/2012 |
| WO | 2014031192 | 2/2014 |
| WO | 2014065901 | 5/2015 |
| WO | 2016032729 | 3/2016 |
| WO | 2016040131 | 3/2016 |
| WO | 2016137838 | 9/2016 |
| WO | 2018136950 | 7/2018 |
| WO | 2019237003 | 12/2019 |

OTHER PUBLICATIONS

International Search Report and Written Opinion of PCT/US2018/014880, dated Jun. 6, 2018.

International Search Report and Written Opinion of PCT/US2018/065396, dated Feb. 24, 2017.

International Search Report and Written Opinion of PCT/US2021/050095 dated Dec. 17, 2021.

(56) References Cited

OTHER PUBLICATIONS

International Search Report and Written Opinion of PCT/US2019/036060 dated Aug. 27, 2019.
International Search Report and Written Opinion of PCT/US2017/053171 dated Dec. 5, 2017.
International Preliminary Report on Patentability of PCT/US2017/053171 completed on Jul. 1, 2019.
Extended European Search Report of European Patent Application No. EP19816177 completed Feb. 2, 2022.
International Search Report and Written Opinion for PCT/US20/046018, dated Oct. 29, 2020.

* cited by examiner

A-A'

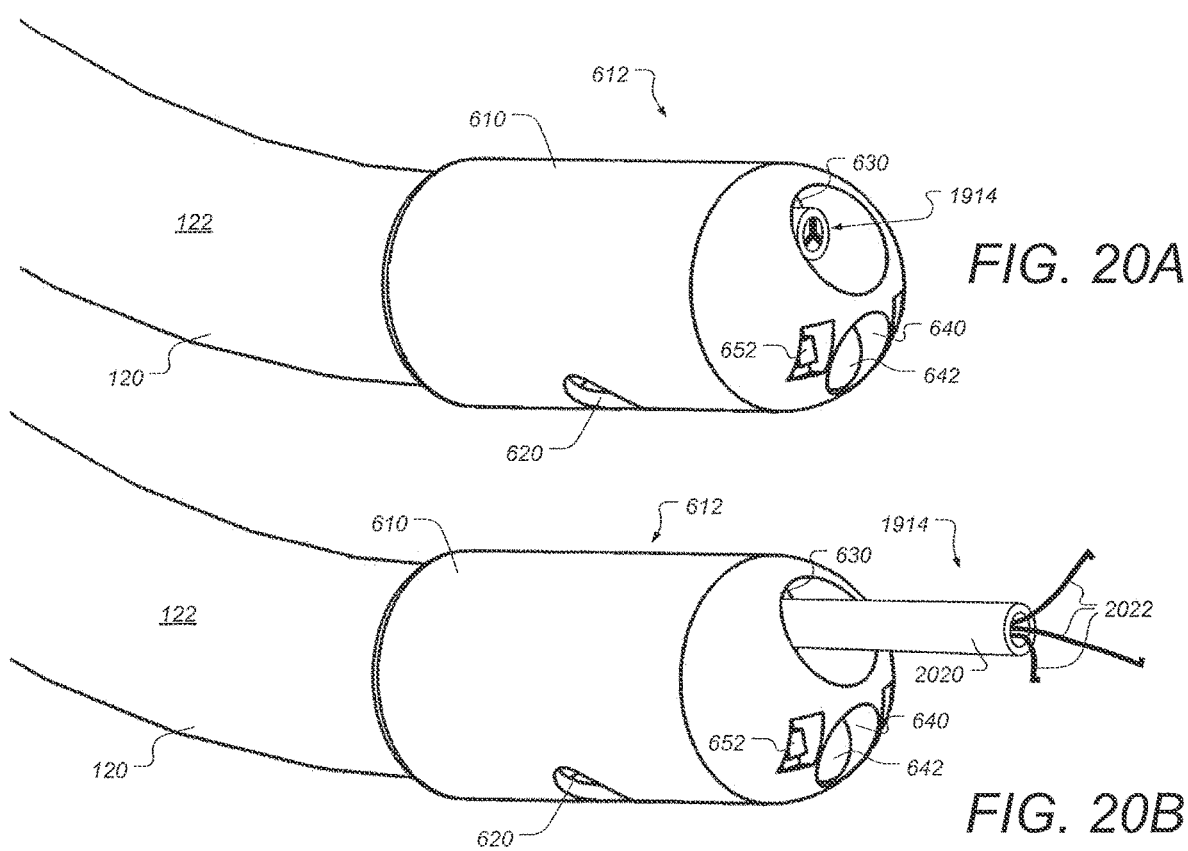

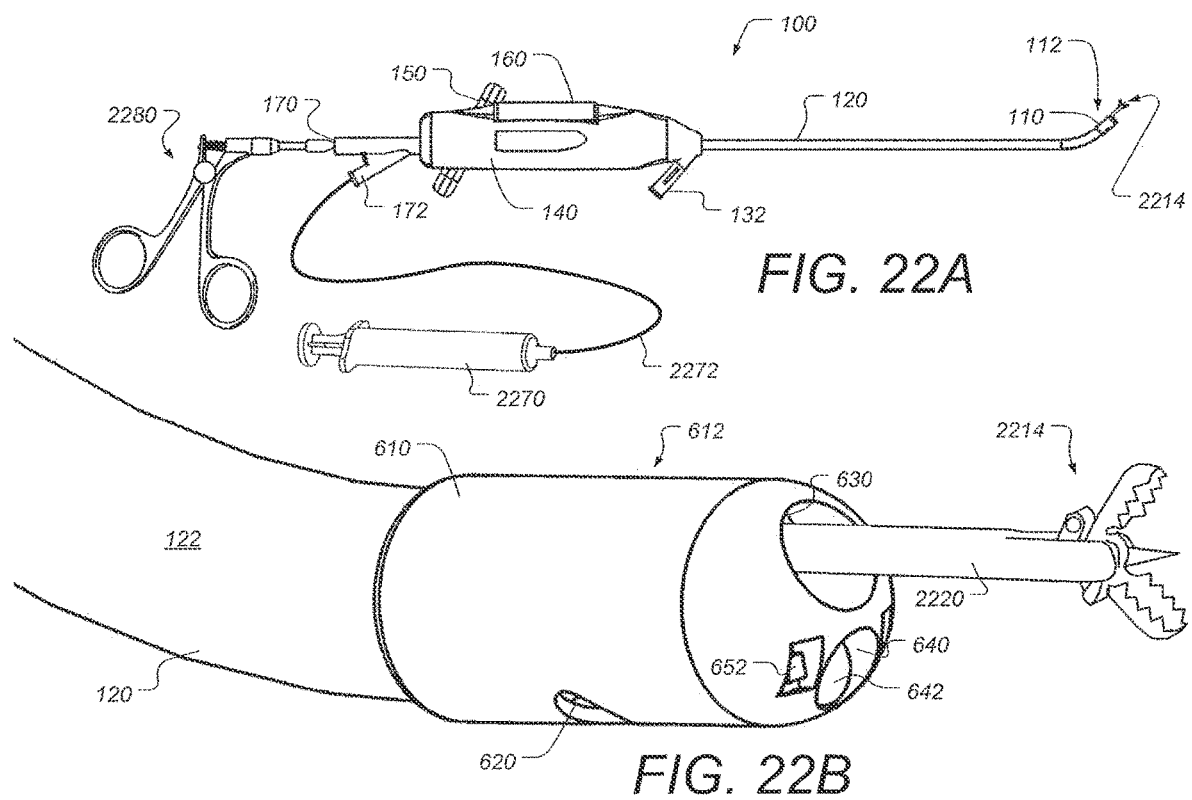

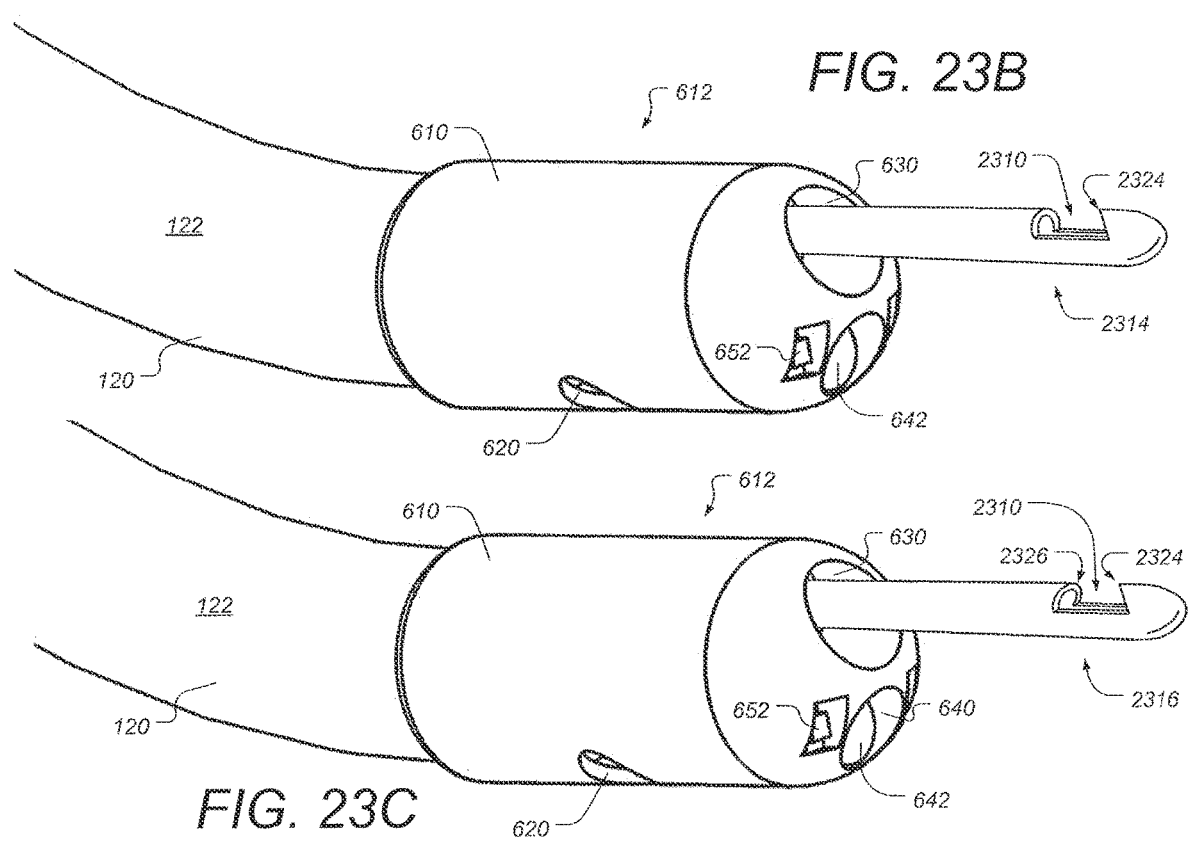

HANDHELD SURGICAL ENDOSCOPE

REFERENCE TO RELATED APPLICATIONS

This patent application is a division of application Ser. No. 16/413,160 filed May 15, 2019 (now allowed and scheduled to issue as U.S. Pat. No. 10,869,592 on Dec. 22, 2020), which is a continuation-in-part of application Ser. No. 16/407,028, filed May 8, 2019, which is a division of U.S. patent application Ser. No. 14/913,867, filed Feb. 23, 2016, which is a national stage entry of PCT application no. PCT/US2016/018670, filed on Feb. 19, 2016, and claims the benefit of and incorporates by reference each of the following provisional applications:
U.S. Prov. Ser. No. 62/119,521 filed Feb. 23, 2015;
U.S. Prov. Ser. No. 62/120,316 filed Feb. 24, 2015;
U.S. Prov. Ser. No. 62/139,754 filed Mar. 29, 2015;
U.S. Prov. Ser. No. 62/254,718 filed Nov. 13, 2015;
U.S. Prov. Ser. No. 62/259,991 filed Nov. 25, 2015;
U.S. Prov. Ser. No. 62/275,222 filed Jan. 5, 2016;
U.S. Prov. Ser. No. 62/275,241 filed Jan. 6, 2016;
U.S. Prov. Ser. No. 62/279,784 filed Jan. 17, 2016; and
U.S. Prov. Ser. No. 62/287,901 filed Jan. 28, 2016.

All of the above-referenced provisional patent applications are collectively referenced herein as "the commonly assigned incorporated applications." The entire contents of the applications identified above are hereby incorporated by reference.

FIELD

This patent specification generally relates mainly to a medical device for use in tissue examinations such as in urology or endoscopic surgery. More particularly, some embodiments relate to an integrated, handheld, low-cost medical device having a single-use portion and one or more multiple-use portions.

BACKGROUND

Conventional endoscopy, or direct vision used to examine the interior of a hollow organ or cavity of the body, uses a complex lens system for transmitting the image for the distal tip of the endoscope to a viewer. The lens system is typically an objective lens plus a relay lens system in the case of rigid endoscopes or a bundle of optic fibers in the case of flexible endoscopes. In the case of both rigid and flexible conventional endoscopes, the lens or fiber optic system is relatively expensive and is intended to be re-used many times. Therefore, stringent decontamination and disinfection procedures need to be carried out after each use.

Disposable endoscopy is an emerging category of endoscopic instruments. In some cases the manufacture of endoscopes can be made inexpensive enough to be used on a single patient only. Disposable or single-use endoscopy lessens the risk of cross-contamination and hospital acquired diseases. Partially disposable endoscopy systems for hysteroscopy are discussed in U.S. Pat. No. 8,460,182, incorporated by reference herein. A hysteroscope having a disposable probe was offered by Endosee Corporation of Los Altos, CA, and is now offered by CooperSurgical, Inc. of Trumbull, CT, a company that acquired EndoSee Corporation.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments that are particularly suitable for fields such as urology and endoscopic surgery rather than hysteroscopy, an endoscope comprises a single-use unit that includes a handle with an opening at a proximal end thereof and a cannula extending along a straight longitudinal axis from the opening and through the handle and distally out of the handle, and which cannula has an imaging module at a distal tip; a multiple-use display unit removably mounted on and supported by the handle and comprising a touch-sensitive display screen; the display unit and the handle include respective mechanical connectors that engage each other to removably mount the display unit on the handle by sliding motion relative to each other; the display unit is to offset from the longitudinal axis when mounted on the handle; the display unit further includes an electrical connector with male pins and the handle further includes an electrical connector with female receptors making electrical contact with the pins as a result of the sliding motion as the display unit is being mounted on the handle; the display unit includes a battery powering the screen and the imaging module; the cannula includes a working channel extending from the opening at the proximal end of the handle to the distal tip of the cannula; the working channel is configured for a surgical device to enter the opening at the proximal end of the handle and pass through the handle along the longitudinal axis; the touch-sensitive screen is configured to respond to touch commands to control taking of images with the imaging module and is further configured to display the images; the cannula further includes a fluid channel with a proximal port that is spaced distally at least 50 mm from the electrical connector of the handle, and a distal port at the distal tip of the cannula; whereby the display unit is removable tool-free from the handle using the sliding motion, for disposal of the handle and cannula after a medical procedure therewith, and is mounted tool-free on a new handle for another medical procedure.

Some embodiments of the instrument further include one of the following elements or features and other embodiments further include two, or three, or more, or all of the following elements or features: (1) the imaging module includes an illumination device and the screen is configured to respond to touch commands to control a degree of illumination by the illumination device; (2) the imaging module includes an imaging device and the screen is configured to respond to touch commands for exposure control of the imaging device; (3) the screen is configured to respond to touch commands to turn on and off the imaging module; (4) the distal tip of the cannula is angled relative to the longitudinal axis; (5) the cannula and the display unit are configured for rotation relative to each other about the longitudinal axis; (6) the endoscope includes wires between the imaging module and an attachment of the display unit to the handle, the wires running in the fluid channel; (7) the touch-sensitive screen is configured to rotate relative to the handle but only about an axis transverse to the longitudinal axis; (8) at least a portion of the handle is elongated and extends along the longitudinal axis; (9) the imaging module and the display unit are configured to communicate with each other when the display unit is not mounted on the handle, the communicating including sending commands from the display unit to the imaging module and receiving images at the display unit taken with the imaging module; (10) the endoscope further includes a tube inserted in said working channel, wherein the surgical device is a grasper tool configured to move in said tube between extended positions in which the grasper tool protrudes distally from the distal tip of the cannula and a retracted position in which the grasper tool is recessed in the working channel of the cannula, the grasper tool having one or more claws configured to enable a biological sample to be taken from the patient's body when the grasping tool is in the extended positions; (11) the surgical device comprises forceps which include jaws configured to be extended to a position in which the jaws protrude distally from the distal tip of the cannula to enable a biological sample to be taken from the patient's body; (12) the surgical device comprises a tubular biopsy tool having a notch at a distal end, wherein a distal end of the notch includes a sharp cutting portion configured to cut a target substance in the patient's body to enable a biological sample to be taken from the patient's body.

According to some embodiments, an endoscope comprises a handle with an opening at a proximal end thereof and a cannula extending along a straight longitudinal axis from the opening and through the handle and distally out of the handle, which cannula has a curving distal tip with an imaging module; a display unit removably mounted on the handle and comprising a touch-sensitive display screen; the display unit and the handle include respective mechanical connectors that engage each other to removably mount the display unit on the handle by sliding motion relative to each other; display unit is off the longitudinal axis when mounted on the handle; the display unit includes a battery powering the screen and the imaging module; the cannula includes a working channel extending from the opening at the proximal end of the handle to the distal tip of the cannula; the working channel is configured for a surgical device to enter the opening at the proximal end of the handle and pass through the handle along the longitudinal axis; the touch-sensitive screen is configured to respond to touch commands to control the imaging module and is further configured to display the images; and the cannula further includes a proximal fluid port that is spaced distally at least 50 mm from the electrical connector of the handle; whereby the display unit is removable tool-free from the handle for disposal of the handle and cannula after a medical procedure therewith and for tool-free mounting on a new handle for another medical procedure.

In some embodiments, the endoscope described in the preceding paragraph further includes one or more of the following elements or features: (1) the cannula further includes a fluid channel communicating with the proximal fluid port, and a distal port of the fluid channel at the distal tip of the cannula; (2) wires running in the fluid channel from the imaging module to the electrical connector of the handle; (3) the cannula's distal tip has a convex distal face with a circumferential periphery that is more curved than a central portion; (4) the distal end of the tip has a convex curvature radius from 4 to less than 7 mm at a central region and from 1 to less than 4 mm at a peripheral area; (5) the handle is free of manual devices controlling operational parameters of the imaging module; (6) a removable cap closing the opening at the proximal end of the handle; (7) a tube inserted in said working channel, wherein the surgical device is a grasper tool configured to move in said tube between extended positions in which the grasper tool protrudes distally from the distal tip of the cannula and a retracted position in which the grasper tool is recessed in the working channel of the cannula, the grasper tool having one or more claws configured to enable a biological sample to be taken from the patient's body when the grasping tool is in the extended positions; (8) the surgical device comprises forceps which include jaws configured to be extended to a position in which the jaws protrude distally from the distal tip of the cannula to enable a biological sample to be taken from the patient's body; (9) the surgical device comprises a tubular biopsy tool having a notch at a distal end, wherein a distal end of the notch includes a sharp cutting portion configured to cut a target substance in the patient's body to enable a biological sample to be taken from the patient's body.

This patent specification further describes an endoscopic method that comprises providing a single-use, disposable unit including the following components that are fixedly assembled into a single unit enclosed in a sterile package configured for disposal after a single use on a patient: a handle shaped and dimensioned to be grasped and manipulated by a user's hand; said handle having a proximal end with an opening and a distal end and further having a mechanical connector and electrical connector both intermediate the proximal and distal ends of the handle; a cannula extending distally from the opening at the proximal end of the handle and passing through the handle and having a working channel extending distally from said opening to a distal tip of the cannula; an imaging assembly and an illumination assembly mounted in the cannula's distal tip. The method further comprises: removing the single-use portion from the sterile package and mounting by hand thereon a re-usable display unit that comprises a touch-sensitive display screen configured to display video images provided by said imaging assembly in the cannula tip and to respond to touch to control imaging operations of the imaging module and display operations on the screen; and inserting the cannula tip into a patient's body; operating said imaging module solely by touch commands entered through said touch-sensitive screen and viewing on the screen images from the imaging assembly.

The method can include one or more or all of the following additional steps of features: (1) inserting a surgical tool along a straight path through said opening at the proximally end of the handle and into at least a proximal portion of said working channel; (2) communicating commands from the display unit to the imaging assembly and receiving at the display unit images from the imaging assembly while the display unit is not mounted on said handle; (3) the single-use unit further includes a tube pre-installed in said working channel, and the surgical tool is a grasper tool having one or more claws and configured to move in said tube between extended positions in which the grasper tool protrudes distally from the distal tip of the cannula and a retracted position in which the grasper tool is recessed in the working channel of the cannula, the method further comprising: manipulating the grasper tool to enable a biological sample to be taken from the patient's body using the claws of the grasper tool when the grasping tool is in the extended positions.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 20A and 20B are side and perspective views of the distal tip and show aspects of the grasper actuation for a handheld surgical endoscope, according to some embodiments;

FIGS. 22A, 22B and 22C show a biopsy tool being used in combination with a handheld surgical endoscope, according to some embodiments; and FIGS. 23A, 23B, 23C and 23D show a biopsy tool being used in combination with a handheld surgical endoscope, according to some other embodiments.

DETAILED DESCRIPTION

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1:
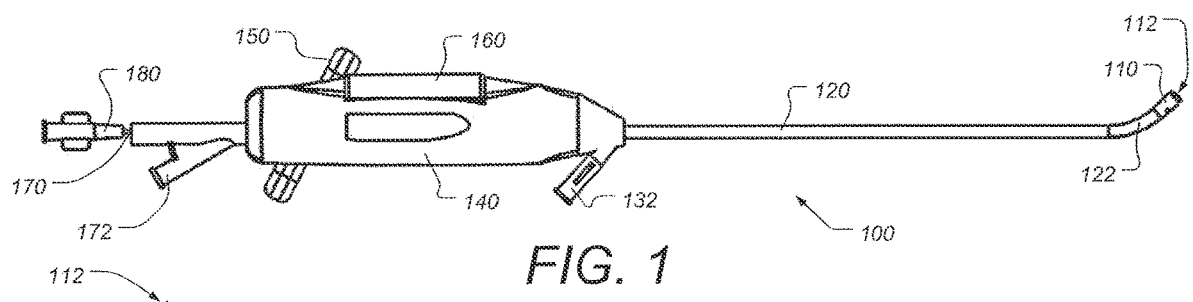
FIG. 1 is a right side view of a handheld surgical endoscope, according to some embodiments.

FIG. 1 is a right side view of a handheld surgical endoscope, according to some embodiments. The endoscope 100 includes an elongated cannula 120 with a distal tip 112 for inserting into a hollow organ or cavity of the body. According to some embodiments, a separate tip sub-assembly 110 is attached to the cannula 120 which can be made from an extruded material. Sub-assembly 110 includes an imaging module and one or more LED light sources for viewing the organ or cavity into which it is inserted. The tip assembly 110 also includes one or more fluid ports, as well as a working channel opening through which a surgical device can protrude. The distal end of the cannula 120 can also be slightly bent as shown in bent region 122.

The endoscope 100 includes a handle portion 140 that is sized and shaped for easy grasping by the endoscope operator (e.g. doctor or other medical professional). According to some embodiments, the cannula 120 includes two or more fluid channels, one of which is fluidly connected to distal fluid port 132 and another that is fluidly connected to proximal fluid port 172. According to some embodiments, one of the channels within the cannula 120 can also be used as working channel and is configured to have a straight path via working channel opening 170. The example shown in FIG. 1 includes a surgical device 180 that enters the working channel via opening 170. It has been found that providing a straight proximal entry port 170 greatly enhances ease of use for inserting various surgical devices.

According to some embodiments, a re-usable display module 150 (FIG. 2) is removably mounted to the handle portion 140 using a connector (not shown), and a rechargeable battery 160 is removably mounted on the upper side of handle portion 140 as shown. According to some embodiments, apart from the display module 150 and battery 160, the entire endoscope device is made at a relatively low-cost and is intended to be disposed of after a single-use. By making the tip, cannula, handle and ports of the device 100 all single-use, stringent decontamination and disinfection procedures as well as the risk of cross-contamination and hospital acquired diseases can be significantly lessened or avoided.

Figure 2:
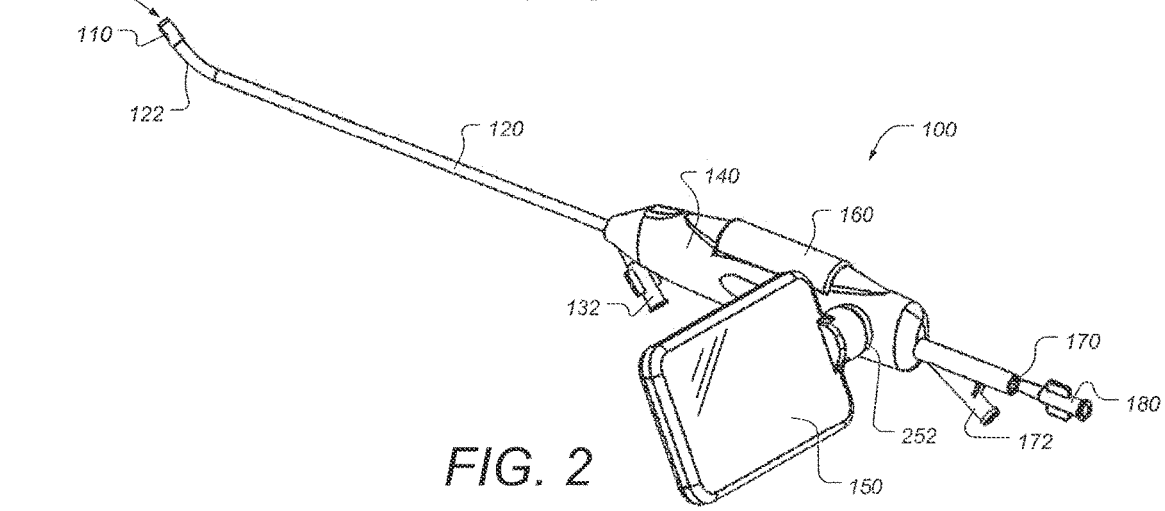
FIGS. 2 and 3 are perspective views of a handheld surgical endoscope, according to some embodiments.
Figure 3:
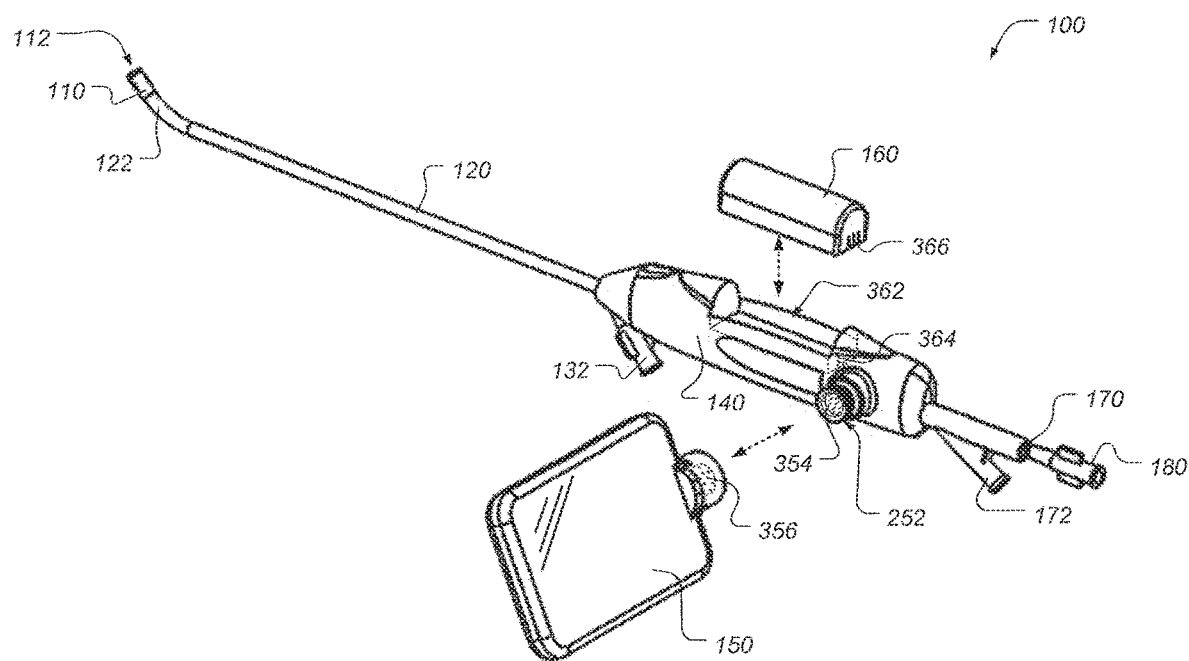

FIGS. 2 and 3 are perspective views of a handheld surgical endoscope, according to some embodiments. Visible in FIGS. 2 and 3 on endoscope 100 is the display module 150 which is removably mounted to the handle portion 140 at the connector 252. Likewise, rechargeable battery 160 is removably mounted into the handle portion 140 via battery socket 362. The connector 252 and battery socket 362 provide both mechanical and electrical connections between the handle portion 140 and the display module 150 and battery 160, respectively. According to some embodiments, a rechargeable battery is included within the display module 150 and therefore a separate battery 160 does not need to be mountable to the handle portion 140. According to yet other embodiments, non-rechargeable batteries are used instead of rechargeable battery 160.

In FIG. 3 the connector 252 is shown in more detail. According to some embodiments, the male portions (e.g. 'pins') 354 protrude from the handle portion 140 and the mating female portions (e.g. 'holes') 356 are recessed in the display module 150. Similarly, for electrical connection between the battery module 160 and handle portion 140 the male portions 364 (e.g. ridges or pins) are positioned on the handle portion 140, while the female portions 366 (slots or holes) are positioned in battery module 160. Providing the male portions of the electrical connectors on the single-use handle portion 140 and the female portions on the re-usable parts—display and battery modules 150 and 160—is beneficial for purposes of decontamination and disinfection. The handle portion 140, cannula 120 and tip 110 together form the single-use portion of the endoscope 100, which is sterilized, for example, during production and is provided to the user in a sealed sterilized packaging. The display module 150 and battery module 160 are intended to be re-used and therefore are subject to decontamination and/or disinfection procedures. In some cases, it is useful to use disposable sterile covers (e.g. clear polyethylene bags or sleeves) to cover the display module 150 and battery module 160 during a surgery or other clinical procedure. In such cases it is preferable for the male portions of the electrical connections to reside on the single-use portion which has been sterilized during manufacture and/or packaging.

Figure 4:
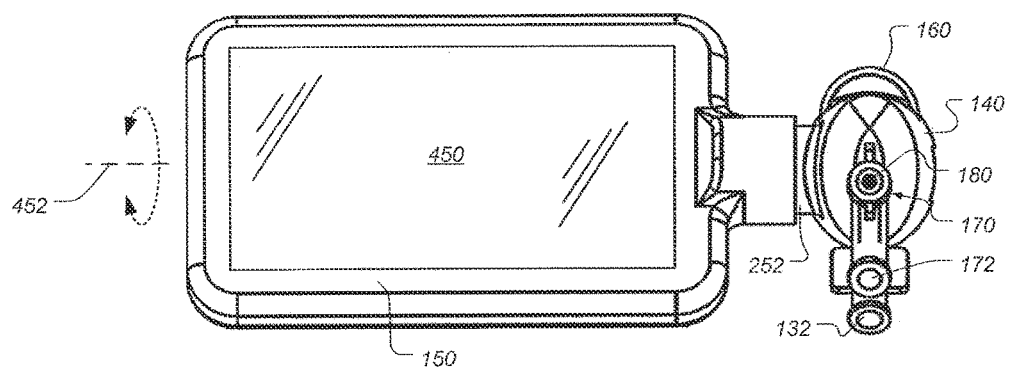
FIG. 4 is a proximal view of a handheld surgical endoscope, according to some embodiments.

FIG. 4 is a proximal view of a handheld surgical endoscope, according to some embodiments. According to some embodiments, the display module 150 includes a large central color display area 450 on which the user can view live images from the camera module mounted on the distal tip 112. According to some other embodiments, the display module 150 is rotatable about axis 452 so as to provide the user with a customizable viewing angle of the display area 450 with respect to the angle of handle 140 and cannula 120. For example, in cases where the handle 140 and cannula 120 are tipped such that the distal tip is lower than the proximal end of the endoscope, the display module 150 can be rotated in the reverse direction so as to maintain an ergonomic viewing angle of display are 450.

Figure 5:
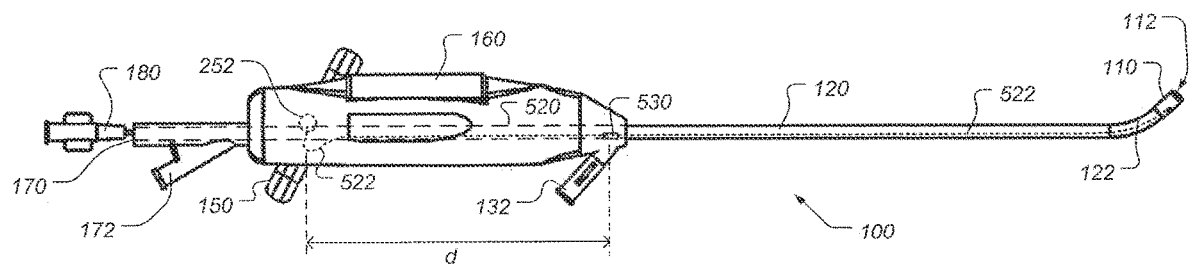
FIG. 5 is a right side view showing further details of a handheld surgical endoscope, according to some embodiments.

FIG. 5 is a right side view showing further details of a handheld surgical endoscope, according to some embodiments. The cannula 120 preferably is made such that it continues through the handle portion 140 to the proximal working channel port 170 as indicated by dashed lines 520. Electrical wires 522 are shown in dotted line which are positioned within one of the fluid channels of cannula 120, until exiting in the vicinity of electrical connector 252. The wires 522 are connected within the distal tip sub-assembly 110 to a camera module and LED light sources (not shown). The distal fluid port 132 can be fluidly connected to one of the fluid channels by way of a cut out 530 in cannula 120. According to some embodiments, the same fluid channel within cannula 120 that is fluidly connected to port 132 is used for carrying the wires 522. It will be appreciated that in this case, adequate fluid sealing should be used to ensure fluid within the shared channel does not leak into the connector 252 where bare, insulated wires, and/or metal contacts are present. Adequate fluid sealing is facilitated by the substantial longitudinal separation distance d measured between the skiving or cut out 530 as shown FIG. 5 (or other fluid exit point from which fluid could travel internally within the handle) to any bare/exposed metal connectors. According to some embodiments, the distance d is 50 mm, 75 mm or even 100 mm. According to some embodiments, the separation distance d is at least 75 mm.

Figure 6A:
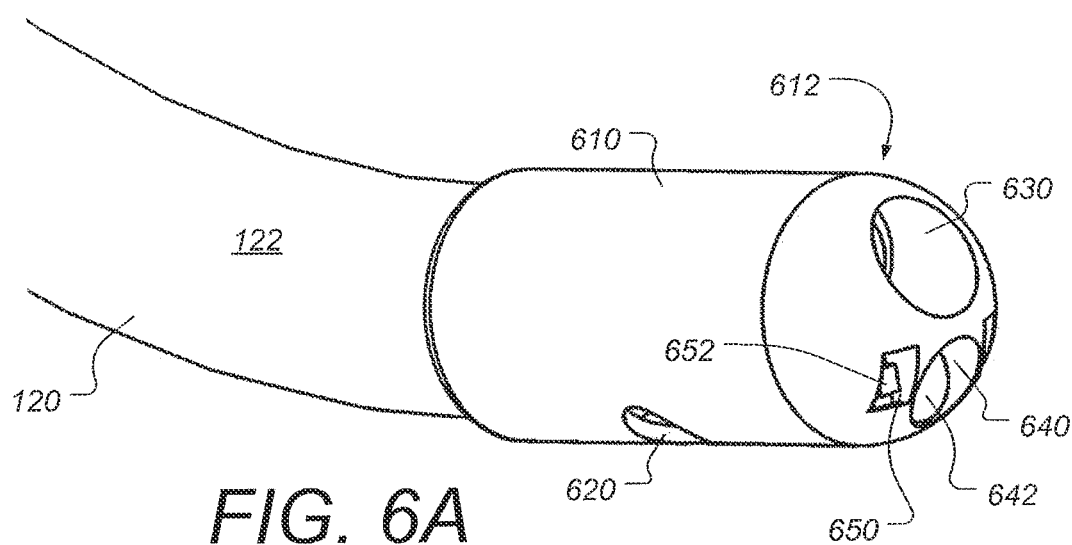
FIGS. 6A-6C are perspective, right side and distal views of a distal tip sub-assembly of a handheld surgical endoscope, according to some embodiments.
Figure 6B:
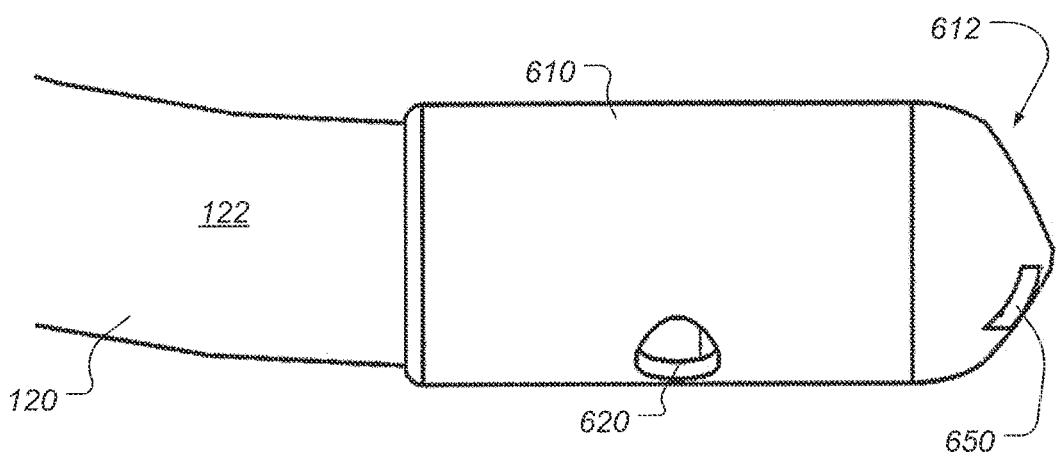
Figure 6C:
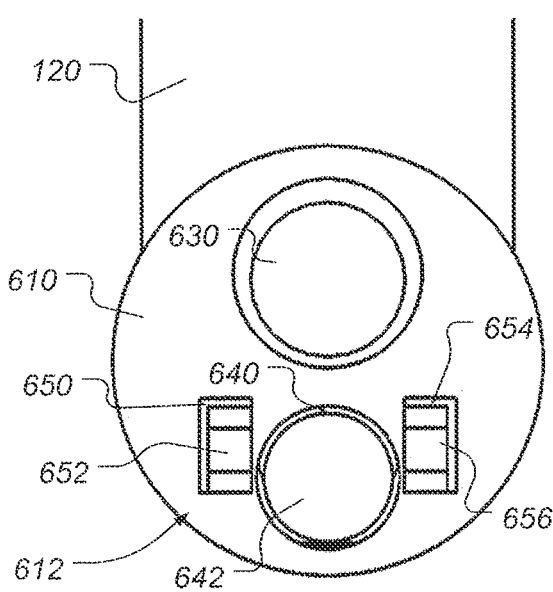

FIGS. 6A-6C are perspective, right side and distal views of a distal tip sub-assembly of a handheld surgical endoscope, according to some embodiments. In this example, the distal sub-assembly 610, which can correspond to tip sub-assembly 110 in FIGS. 1-5, is shown with a spherically rounded distal tip 612. The assembly 610 includes a working channel port 630 through which a surgical instrument can pass. The tip 612 also includes a camera port 640 from which imaging module 642 can view the organ or cavity into which the endoscope is inserted. Also visible are light ports 650 and 654 through which LEDs 652 and 656 shine light to illuminate the organ or cavity being imaged using imaging module 642. According to some embodiments, illumination can be achieved using techniques other than LEDs. For example a light fiber guide or pipe can be used to transmit light from a light source in handle 140 (or some other proximal location). According to some embodiments, two lower fluid ports are provided, of which one, port 620, is visible in FIGS. 6A and 6B. In the case there are two fluid channels within cannula 120, an upper fluid channel can be combined with the working channel to provide fluid in-flow (i.e. flowing fluid out of the device and into the patient's organ or cavity). A lower fluid channel within cannula 120 can be used to provide fluid out-flow (i.e. flowing fluid out of the patient's organ or cavity and into the device) via the bottom mounted fluid ports (of which port 620 is visible). As described with respect to FIG. 5, supra, this lower fluid channel can also be used to carry wires that are connected to the imaging module 642 and LEDs 652 and 656. As mentioned, the tip 612 is spherically rounded, for example having radius close to or equal to the half the width of the cylindrical portion of the tip assembly 110. It has been found that a highly rounded, or spherical tip shape such as shown can be beneficial in providing a smooth contour which reduces or eliminates injury to the patient's tissues in some applications.

Figure 7:
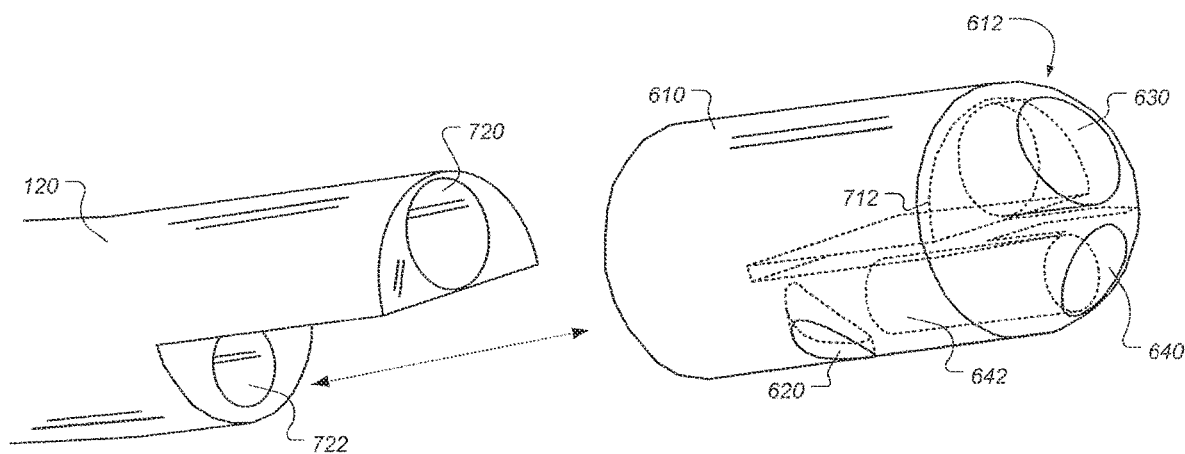
FIG. 7 is a perspective view of a cannula and tip sub-assembly of a handheld surgical endoscope, according to some embodiments.

FIG. 7 is a perspective view of a cannula and tip sub-assembly of a handheld surgical endoscope, according to some embodiments. As described, supra, cannula 120 can be extruded and contain two fluid channels. In the example shown cannula 120 has an upper lumen 720 and a lower lumen 722. Although both upper and lower lumen 720 and 722 are shown in FIG. 7 with a circular cross section, according to some embodiments other cross sections can be used. It has been found that the manufacture of a dual lumen extruded cannula is simple and straightforward. Prior to joining the lumen to the tip sub-assembly 610, a simple 90 degree cut is made in the distal end of cannula 120, leaving a "D" shaped upper half as shown. The D shaped upper half mates with a D shaped recess in the upper half of subassembly 610. The recess includes a stop 712. In this way the D shaped portion of the cannula 120 is "keyed" with the tip assembly 610 such that it is easy to rotationally and longitudinally align the cannula 120 and the tip sub-assembly 610. Thus the process of joining the tip 610 to cannula 120 is relatively simple and straightforward. Note that even with the dual lumens, plenty of material remains in cannula 120 to provide structural integrity. The location of the imaging module 642 is also shown in FIG. 7.

Figure 8A:
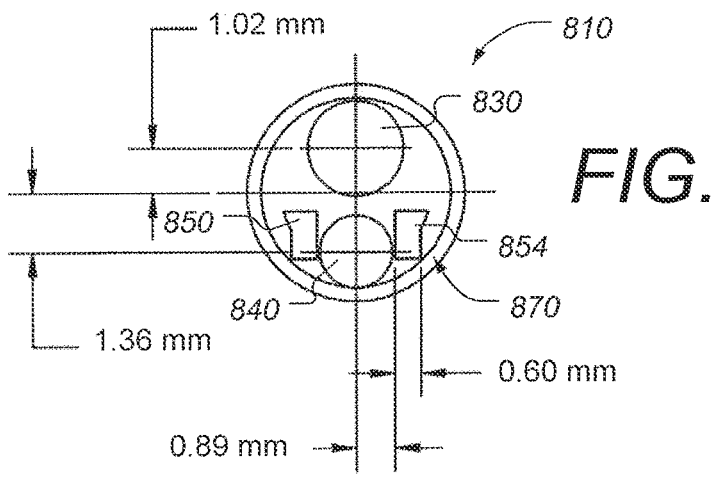
FIGS. 8A-8E are distal, proximal, cross-sectional, bottom and perspective views of a distal tip housing of a handheld surgical endoscope, according to some embodiments.
Figure 8B:
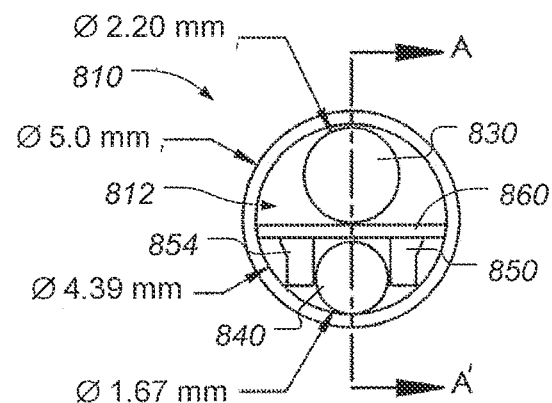

FIGS. 8A-8E are distal, proximal, cross-sectional, bottom and perspective views of a distal tip housing of a handheld surgical endoscope, according to some embodiments. The tip housing 810, for example, can be used to house the components of the distal tip subassembly 110 shown in FIGS. 1-3 and 5. The tip housing 810 has a rounded outer distal edge, such as tip 610 shown in FIGS. 6A-6C and 7. In contrast, however, the central distal portion of the tip housing 810 is flatter and less rounded than tip 610. According to some embodiments, the tip housing 810 is formed by molding and is made from a material such as acrylic, although other suitable materials can be used. FIGS. 8A and 8B are distal and proximal views, respectively, of the tip housing 810. The dimensions of the outer circumference and proximal opening 812, as well as the dimensions and positioning of the working channel port 830, camera port 840, light ports 850 and 854, and shelf 860 according to some embodiments, are shown. Note that in the example shown in FIG. 8B, the camera module is positioned in port 840 which is 1.67 mm in diameter. According to some embodiments, other camera module sizes are used, such as a 1.4 mm diameter camera module. In such cases, the space within the molded tip housing 810 is changed accordingly.

Figure 8C:
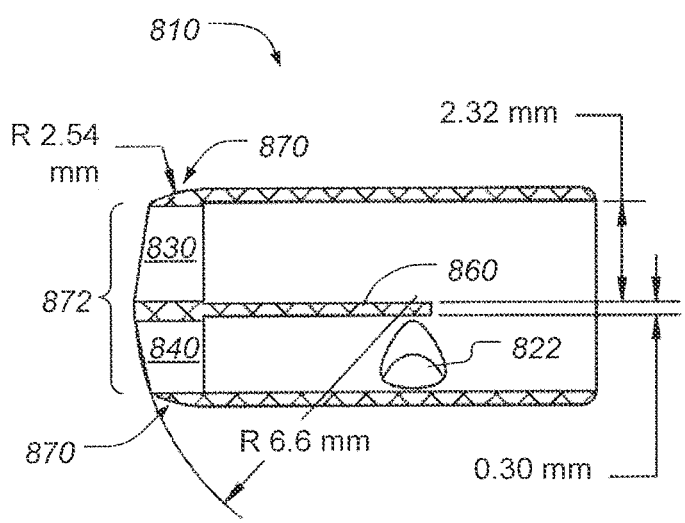
Figure 8D:
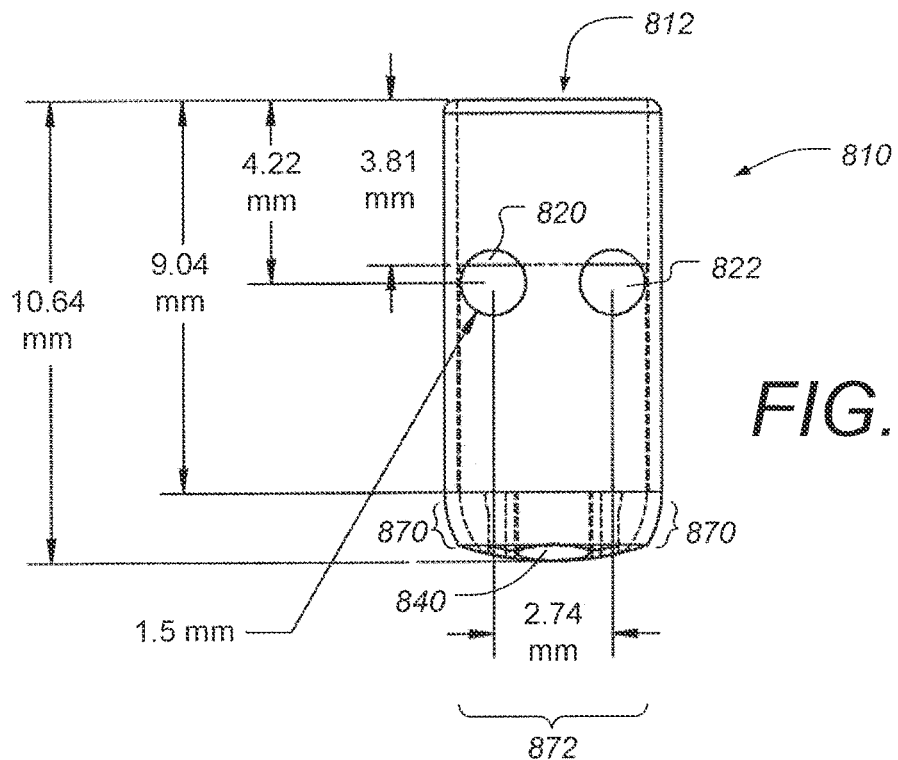
Figure 8E:
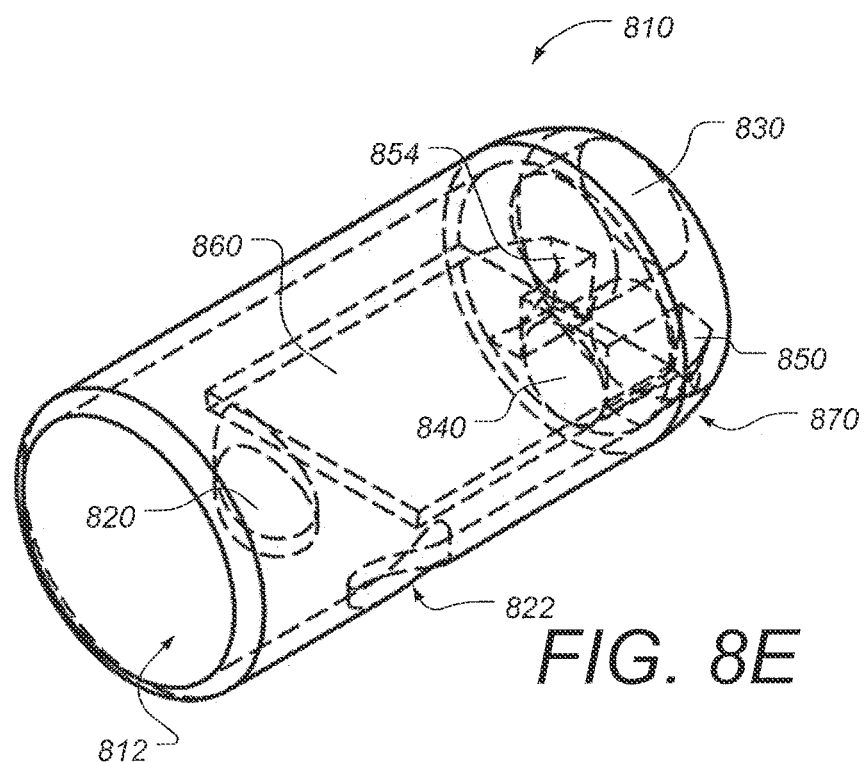

FIG. 8C is a cross sectional view of the distal tip housing along A-A' (shown in FIG. 8B). As can be seen, the outer distal edge 870 of the tip housing 810 is rounded to a radius of 2.54 mm. According to some embodiments, the distal outer edge 870 is also rounded to be spherical in shape. It has been found that especially in the case of inserting the endoscope into and through passages such as the urethra, trachea or blood vessels, it is desirable that the outer distal edge 870 of the distal tip should be rounded since that region of the distal tip both contacts and dilates the tissue passage. In such cases, the central portion 872 of the distal tip can be made less rounded or even flat. Making the central portion 872 less rounded or flat has been found to enhance imaging characteristics over a more spherical overall tip shape (such as shown in FIGS. 6A-6C and 7) since the camera and illumination is not or significantly less impaired. In the case of a spherical overall tip shape (such as shown in FIGS. 6A-6C and 7) where the central portion of the distal tip is rounded to close the radius of the cylindrical portion of the shaft and/or tip, the camera view from the camera port and/or the illumination from the light ports can be partially blocked by the rounded distal tip. In the example shown in FIGS. 8A-8C, the central portion 872 of the distal tip is rounded spherically to a radius of about 6.6 mm. According to some embodiments, other rounding shapes are possible while still providing good tissue contact properties and good illumination and viewing properties. For example, the outer distal edge can be rounded spherically to a radius of between 1 mm to 3.5 mm, while the central portion (which includes most or all of the camera and light ports) is either flat or rounded spherically to a radius of greater than 4 mm. Also visible in FIG. 8C is the proximal opening 812 and shelf 860 which are shaped to accept the distal end of extruded cannula 120 (such as shown in FIGS. 7 and 10B). One of the two lower fluid ports 822 is also visible, which can provide fluid out-flow (flowing out of the patient and into the cannula). In FIG. 8D, the dimension and positioning of the two lower fluid ports 820 and 822 are visible. FIG. 8E is a prospective view of the molded distal tip housing 810. According to some embodiments, more than two lower fluid ports are provided for fluid out-flow (flowing out of the patient and into the cannula).

Figure 9:
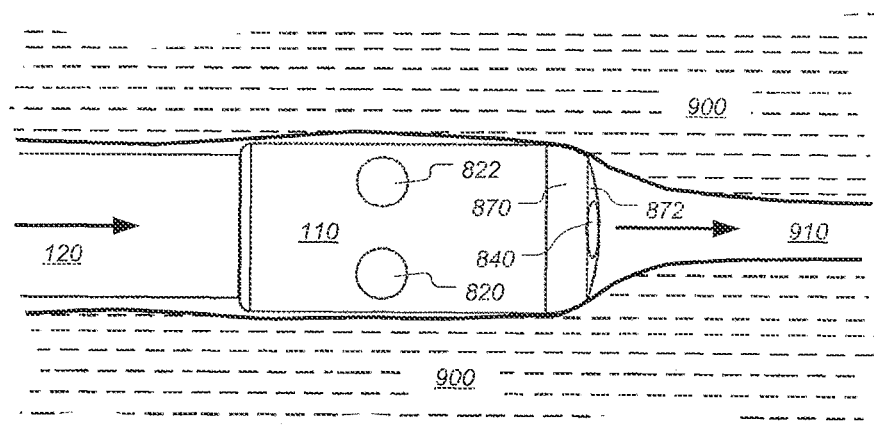
FIG. 9 is a diagram showing a handheld surgical endoscope being inserted in a tissue passageway, according to some embodiments.

FIG. 9 is a diagram showing a handheld surgical endoscope being inserted in a tissue passageway, according to some embodiments. The distal tip 110 and cannula 120 of a surgical endoscope such as shown in FIGS. 1-5 is being inserted in passageway 910 within tissue 900. As shown the passageway 910 is being dilated by the distal tip 110. The distal tip 110 has a hybrid rounded shape such as shown in FIGS. 8A-8E such that its outer distal edge 870 is more rounded (i.e. smaller rounding radius) than the central portion 872 of the distal tip. As discussed, supra, this hybrid rounding profile allows for both good tissue contact and dilation characteristics, and good viewing and illumination characteristics.

Figure 10A:
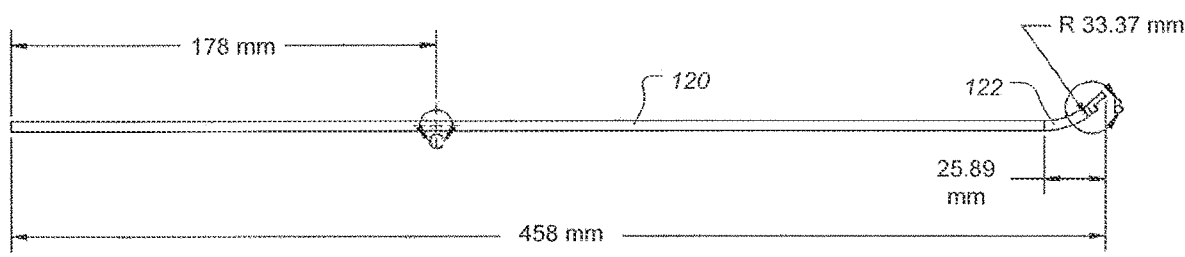
FIGS. 10A-10C are side views showing further detail of a cannula used with a handheld surgical endoscope, according to some embodiments.
Figure 10C:
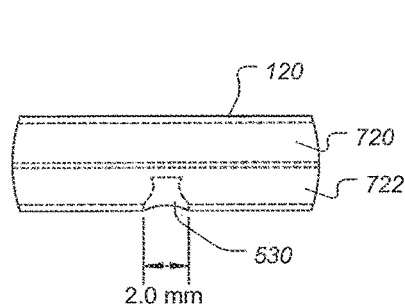
Figure 10B:
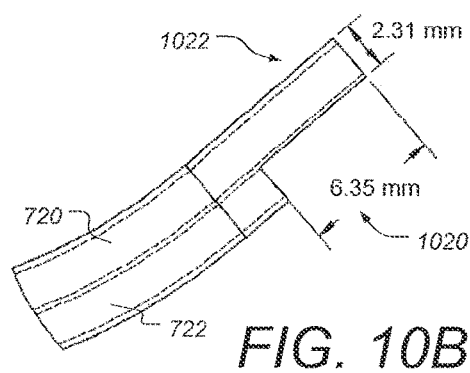

FIGS. 10A-10C are side views showing further detail of a cannula used with a handheld surgical endoscope, according to some embodiments. FIG. 10A is a side view showing example dimensions and shape of cannula 120 used in the handheld endoscope 100 shown in FIGS. 1-5. The cannula 120 can be extruded and made of a nylon material such as nylon 12 (e.g. Grilamid® L25). The distal end of cannula 120 can include a bent region 122 which is beneficial for certain applications and can effectively increase the field of view of the camera fixed to the distal tip when the endoscope is rotated about its central longitudinal axis. FIG. 10B shows further detail of the distal end of the extruded cannula 120. As discussed with respect to FIG. 7, a simple 90 degree cut can be used to form the cut-away region 1020 while leaving a D shaped upper portion 1022. Also shown in dotted outline are the upper and lower lumens 720 and 722. FIG. 10C shows a further detail in the mid-shaft region where cut out 530 is made to make a fluid connection between lower lumen 722 and a distal fluid port (such as distal fluid port 132 shown in FIGS. 1-5). Note that while FIG. 7 shows the cannula 120 being mated to spherically tipped distal tip 610, according to some embodiments, the cannula 120, which is shown in detail in FIGS. 10A-10C and 11A-11B, can also be mated to a hybrid-rounded distal tip shape such as shown in FIGS. 8A-8E and 9. According to some embodiments, the cannula 120 can be made such that its stiffness is not constant along its length. For example, it may be useful in some clinical applications to provide a cannula that is more flexible towards the distal tip and stiffer towards the handle. In such cases the cannula 120 can be made from a multi-durometer tubing such as a multi-duro Pebax® or Grilamid®.

Figure 11A:
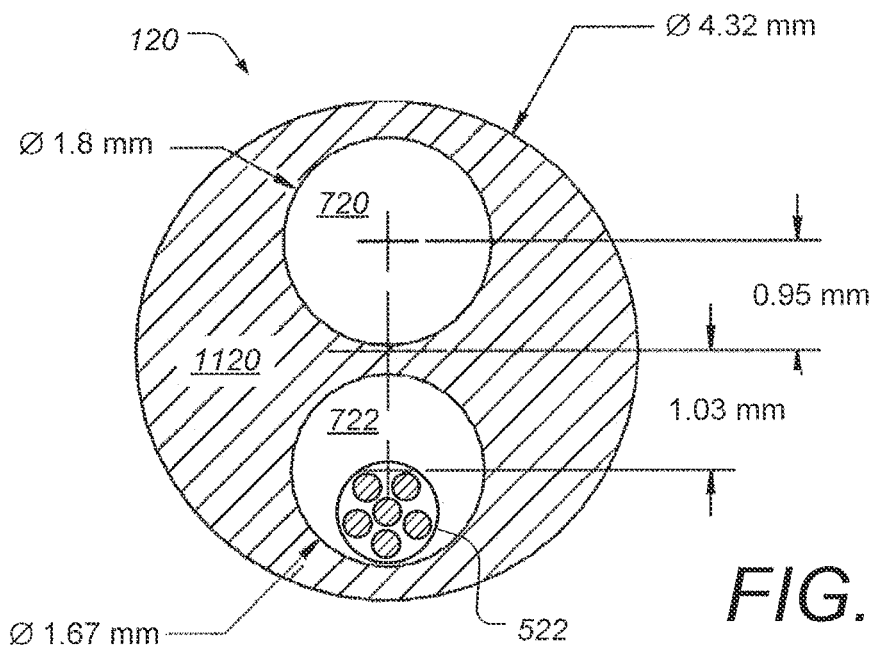
FIGS. 11A and 11B are cross sectional views showing further detail of cannulae used with a handheld surgical endoscope, according to some embodiments.
Figure 11B:
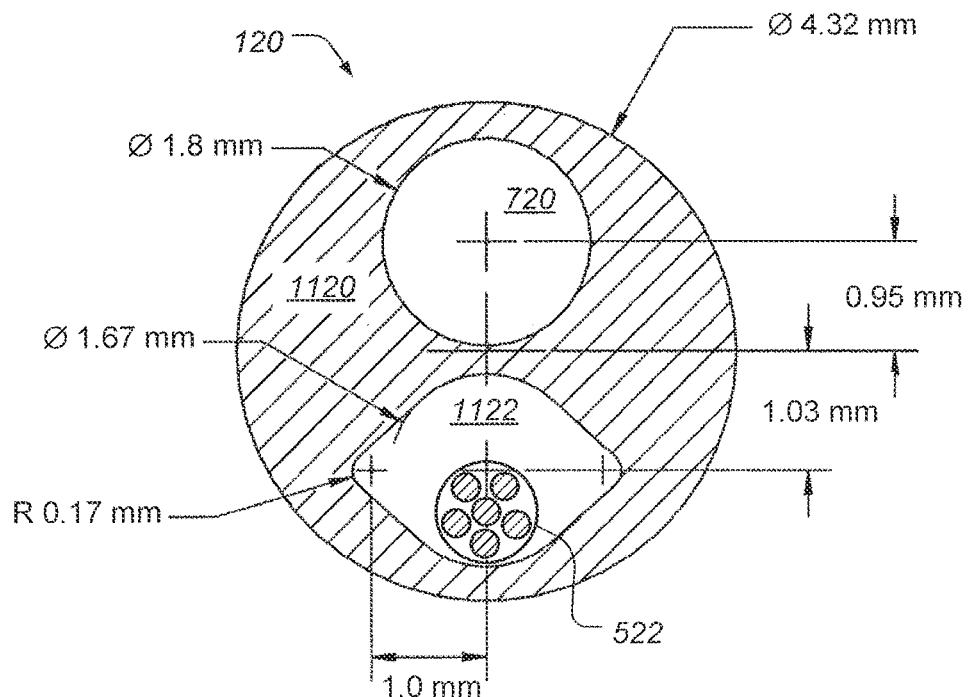

FIGS. 11A and 11B are cross sectional views showing further detail of cannulae used with a handheld surgical endoscope, according to some embodiments. In FIG. 11A, positions and dimensions of upper and lower lumens 720 and 722 are shown formed within cannula material 1120. Also visible are electrical wires 522 positioned within the lower lumen 722. Note at wires 522 in this case include six conductors for connection to the camera and LEDs on the distal tip sub-assembly, although other numbers of conductors could be used. In cases where a larger cross-sectional area of the lower lumen is desired that is not occupied by the wires 522, other shapes can be used such as shown in FIG. 11B. In FIG. 11B, the lower lumen 1122 has a non-circular cross-section so that greater fluid carrying capacity can be provided while still accommodating the wires 522.

It has been found that forming the cannula and distal tip parts separately has significant manufacturing advantages. The cannula can be extruded while the distal tip can be molded. Furthermore post-extrusion preparation of the extruded cannula is very straightforward, using only simple cuts made mid shaft (shown in FIG. 10C) and distal end (shown in FIG. 10B). Also, it has been found that using two lumens as shown in FIG. 11A or 11B, there is plenty of material remaining to provide suitable structural integrity for the cannula. Having two lumens has been found to be suitable for providing separate fluid in-flow and out-flow channels, as well as sufficient space for the video and illumination wires and a working channel.

Figure 12A:
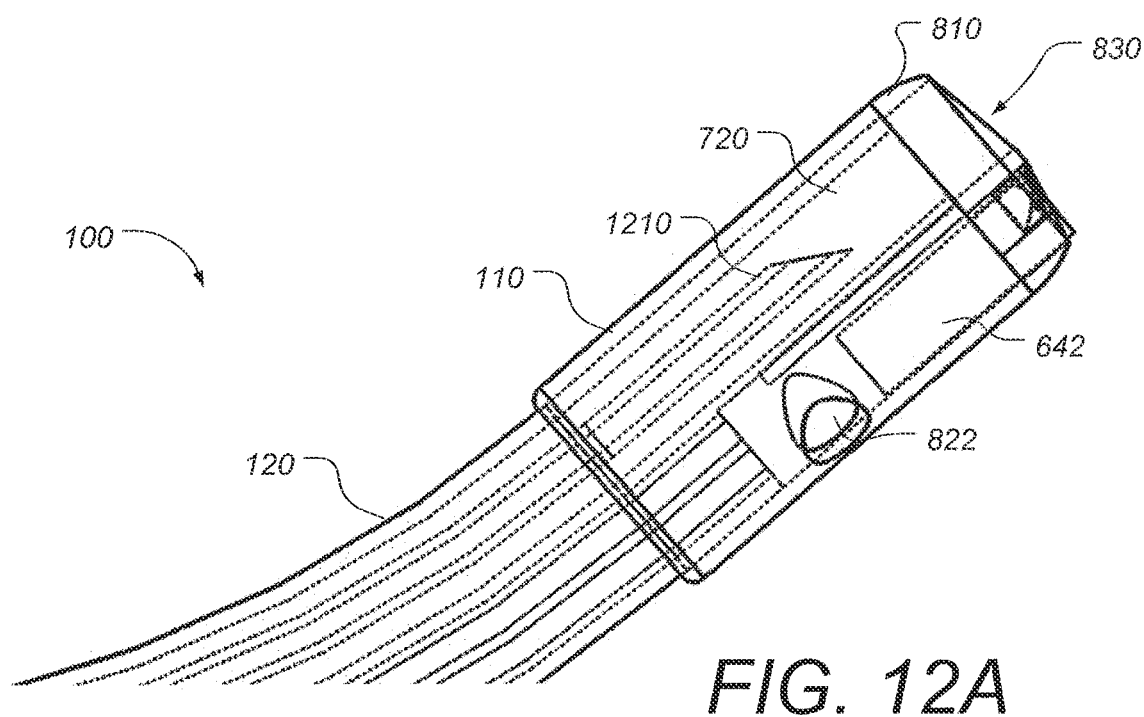
FIGS. 12A-12D are side and perspective views illustrating a procedure in which a surgical device is pre-installed within a handheld surgical endoscope, according to some embodiments.
Figure 12B:
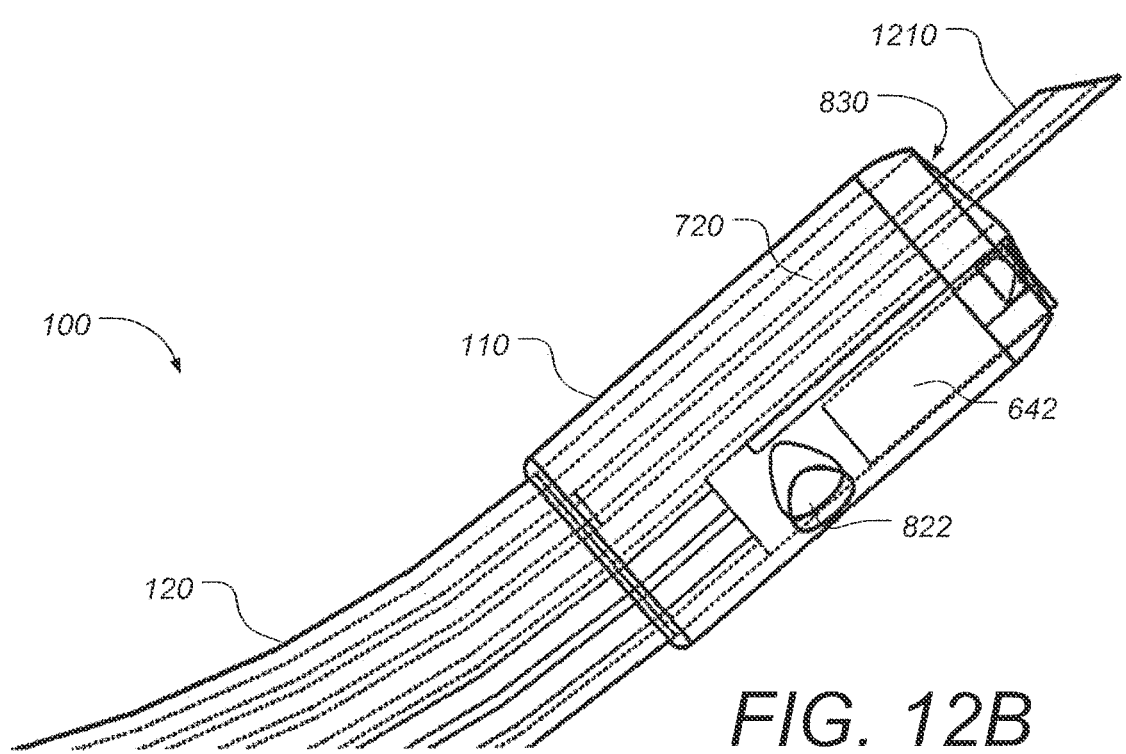
Figure 12C:
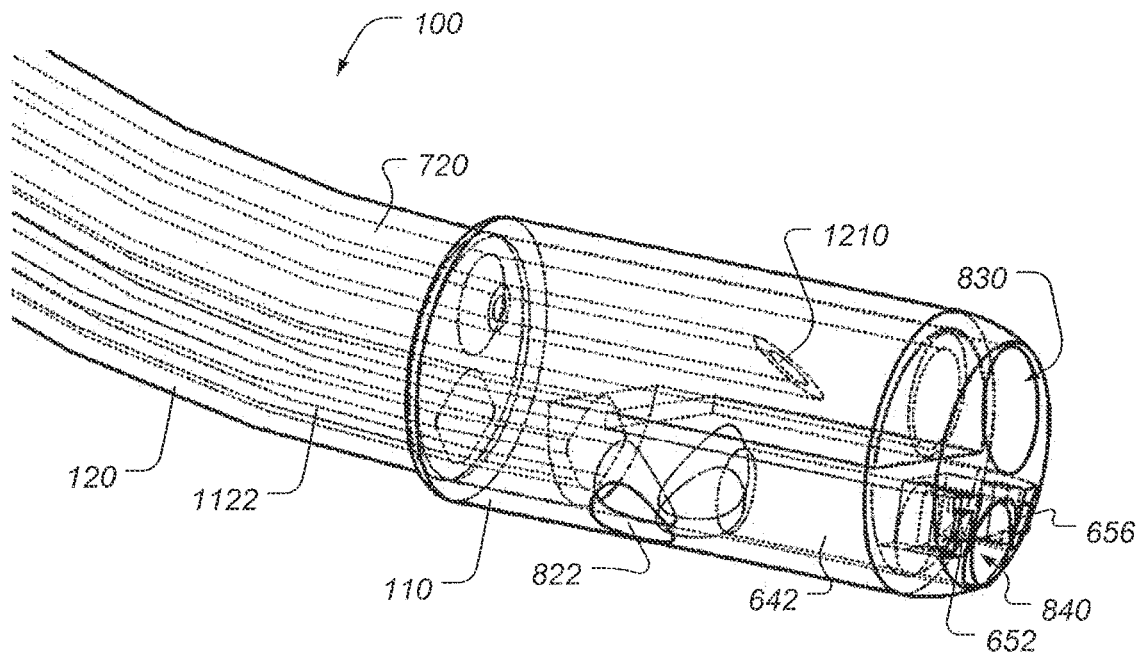
Figure 12D:
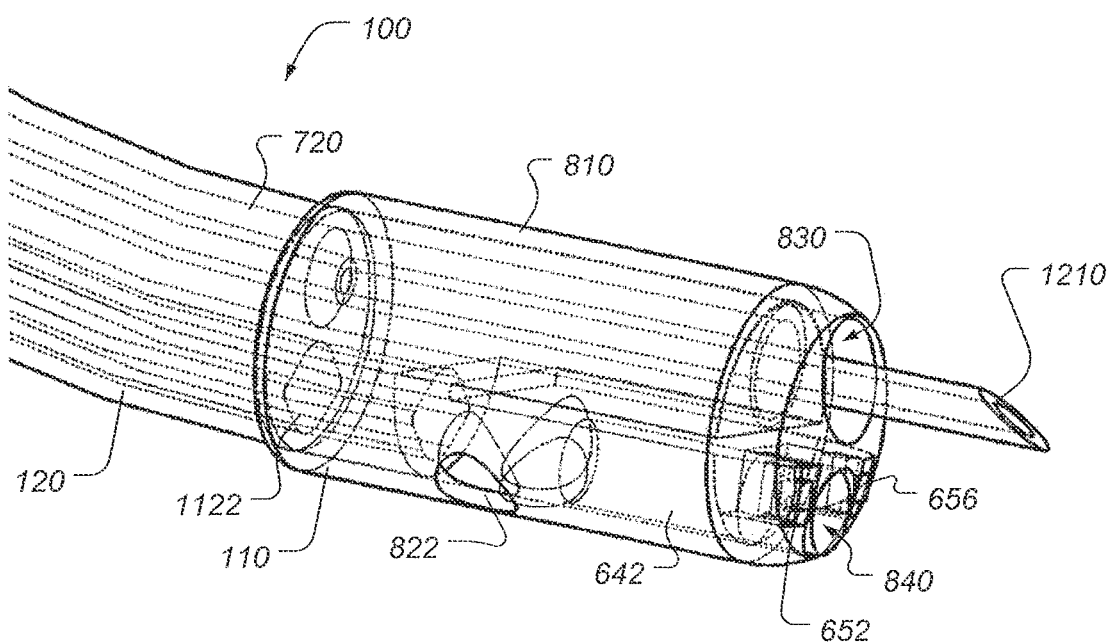

FIGS. 12A-12D are side and perspective views illustrating a procedure in which a surgical device is pre-installed within a handheld surgical endoscope, according to some embodiments. In FIGS. 12A and 12C, a needle 1210 is shown positioned within the upper lumen 720 of endoscope 100 which is being used as a working channel. According to some embodiments, the needle 1210 is installed into the position shown in FIGS. 12A and 12C prior to insertion of the endoscope 100 into the patient. For example, the needle 1210 could be installed into the endoscope 100 in the clinic or doctor's office in preparation for the medical procedure. According to some other embodiments, the needle 1210 or other surgical implement is pre-installed in the cannula as shown during manufacture (e.g. on the production line) or otherwise, prior to sterile packaging of the single-use portion of the endoscope 100. While in the position shown in FIGS. 12A and 12C, the distal tip 110 of endoscope 100 is inserted into the patient (such as shown in FIG. 7). After the distal tip 110 is positioned in the desired location (e.g. in the desired hollow organ or cavity of the body), the needle 1210 is pushed into the patient's tissue. FIGS. 12B and 12D show side and perspective views, respectively, of the needle 1210 protruding from the working channel port 830 of the distal tip 110. In the case where needle 1210 is a hollow needle (e.g. hypodermic needle), than the needle 1210 can be used to inject substance into the penetrated tissue and/or extract fluids from it. Note that in FIGS. 12A-12D the distal tip 110 has a hybrid rounded shaped tip housing 810 such as shown in FIGS. 8A-8E, having its outer distal edge more rounded than the central portion of the distal tip. A non-circular lower lumen 1122 is shown in this case. Imaging module 642 and LEDs 652 and 656 are also shown positioned within tip 110.

Figure 13:
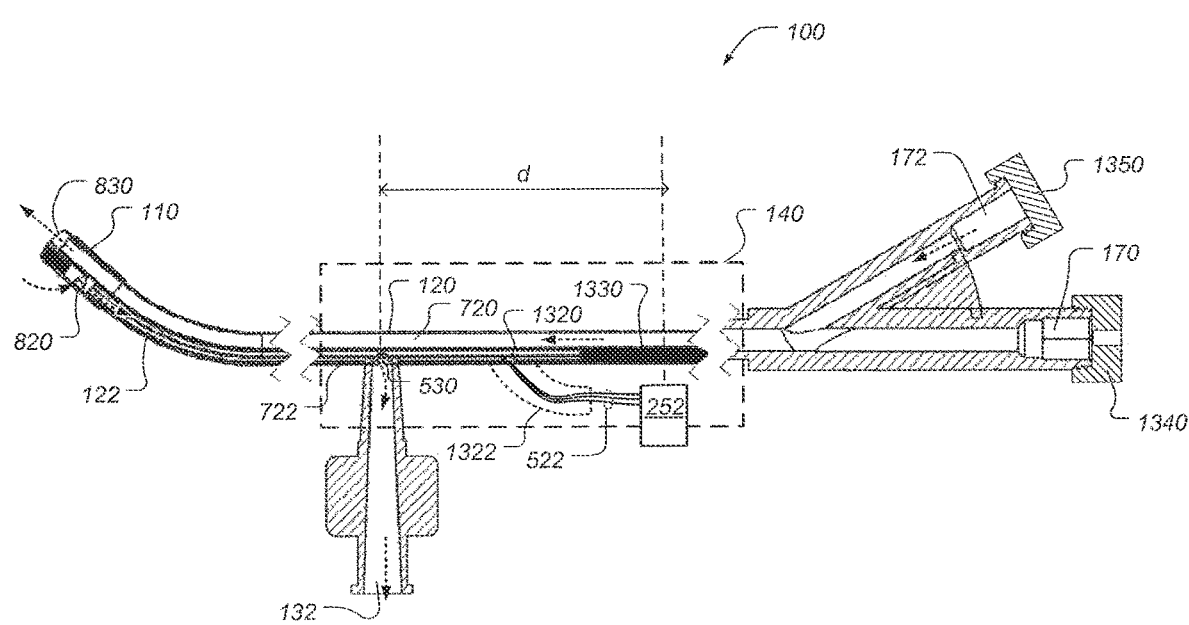
FIG. 13 is a schematic diagram illustrating various aspects of a handheld surgical endoscope, according to some embodiments.

FIG. 13 is a schematic diagram illustrating various aspects of a handheld surgical endoscope, according to some embodiments. The cannula 120 is shown with upper fluid lumen 720 and lower fluid lumen 722. For clarity the handle 140 is not shown in detail but is functionally marked with a dashed rectangle. As can be seen, the upper lumen 720 is in fluid communication with proximal fluid port 172, working channel opening 170 and distal working channel port 830. The upper fluid lumen 720 is configured to be used for both passage of a surgical instrument and for fluid in-flow. The fluid in-flow path is from proximal fluid port 172, through lumen 720, out of tip 110 via distal working channel port 830 and into the patient, as shown by the dashed arrows. Passage of a surgical device (e.g. a needle) through lumen 720 is via working channel opening 170. On the proximal end of surgical endoscope 100 a wiper 1340 is shown attached to working channel opening 170 and a cap 1350 is shown attached to proximal fluid port 172. When fluid port 172 is being used for introducing fluid into the patient, a syringe or other suitable device would be connected to port 172 instead of a cap. When a surgical instrument is being introduced through opening 170 then a wiper, such as wiper 1340, can be used which has an opening to allow for passage of the instrument. According to embodiment a duckbill valve can be provided in addition to or instead of wiper 1340, although a properly sized wiper will generally form better fluid seal than a duckbill when an instrument is present. When an instrument is not present a cap, such as cap 1350 can also be used on opening 170. Note that in FIG. 13, proximal fluid port 172 is shown angled slightly upwards instead of downwards as shown in other figures such as FIGS. 1-5, 14, 15B and 16. In general, the orientation of the fluid ports 132 and 172 (downwards, upwards or to a side) is a matter of design choice depending upon ergonomic and other considerations of the expected clinical application.

The lower fluid lumen 722 is configured to be used for both carrying the wires 522 as well as for fluid out-flow. The fluid out-flow path, also shown by dotted arrows, is out of the patient, through the two lower fluid ports 820 and 822 (of which only port 820 is visible), through lower lumen 722, through cut out 530 and out through distal fluid port 132. Note that although the fluids carried by the lumens 720 and 722 is often a liquid, in some embodiments one or both lumens can be used to carry gas (e.g. $CO_2$) or a mixture of liquid and gas. The wires 522 pass from the camera and LEDs in the distal tip 110, through lumen 722, out through cut out 1320 to connector 252. Note that between the cut out 1320 and connector 252 the wires 522 still reside within the handle 140. According to some embodiments a sealant 1322 is used within the handle 140 to prevent any fluid from passing within the handle 140 from lumen 722 to the connector 252 where liquid could cause a short or other malfunction by contacting bare wires or un-insulated connectors. Lumen 720 is also blocked by sealant 1330 to prevent any fluid from exiting distally into the handle 140. Note that sealing, such as using sealant 1322 and 1330 is used to prevent fluid leaking from lumen 722 into internal portions of the handle 140. In general, liquid leaking inside the handle 140 towards bare/un-insulated metal contacts or wires can be more troublesome than liquid traveling outside the handle 140 (such as dripping from openings 170 or 172) since such liquid is not visible. To prevent such internal leaks, an adequate distance d is provided where the distance d is measured between internal fluid cut out 530 or other point where fluid could leak internally to bare/uninsulated metal (such as connector pins, sockets, bare wire portions) and connector 252.

Figure 14:
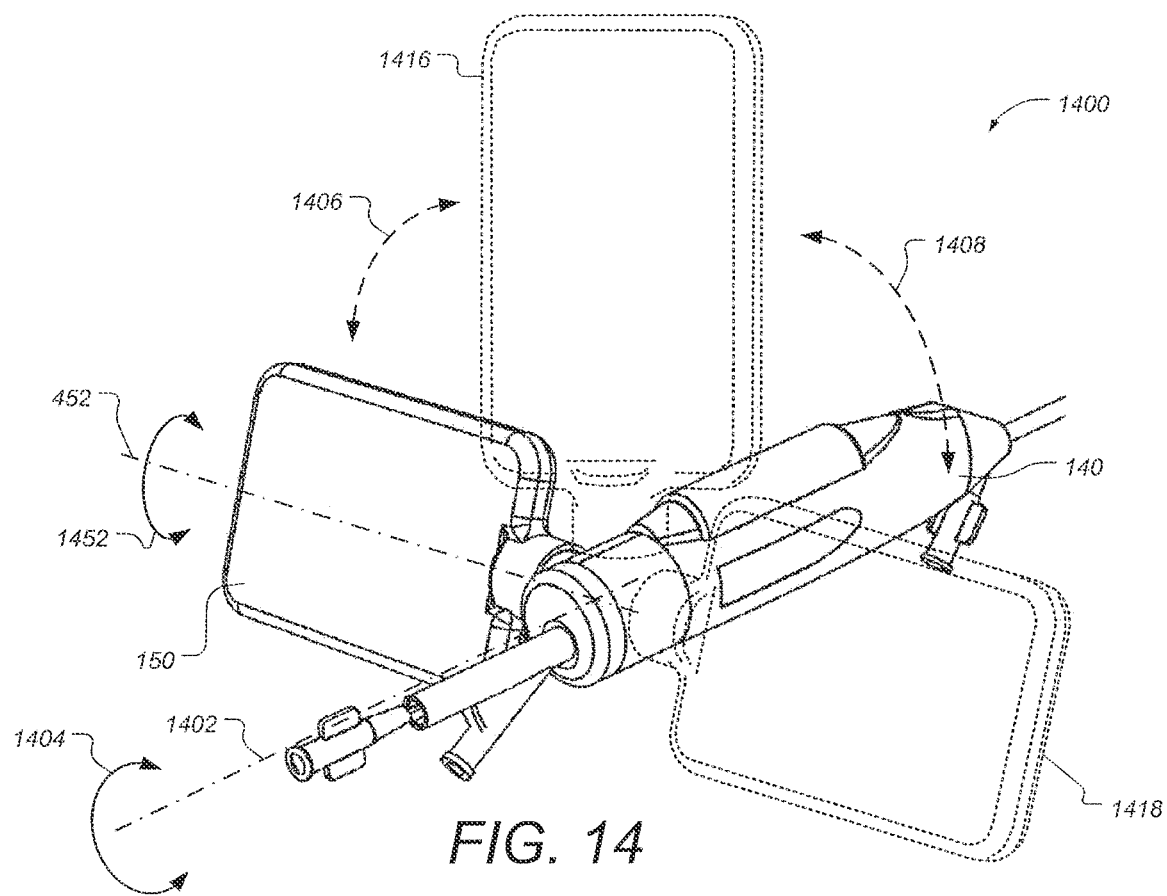
FIG. 14 is a perspective view of a handheld surgical endoscope, according to some embodiments.

FIG. 14 is a perspective view of a handheld surgical endoscope, according to some embodiments. The display module 150 is rotatable about axis 452 as shown by arrow 1452 and as depicted supra, e.g. in FIG. 4. In addition, however, in the case shown in FIG. 14 the display module 150 is also rotatable about the handle's longitudinal axis 1402 as shown by solid arrow 1404 and dotted arrows 1406 and 1408. Example alternate positions for display module 150 are shown in dotted outlines 1416 and 1418. The positioning of the display module 150 at position 1418 can be particularly ergonomic in some cases, such as where the operator is left handed. In other cases the entire endoscope 1400 is sometimes rotated about axis 1402 while performing the surgical procedure or inspecting tissues. For example, rotating the endoscope about axis 1402 can effectively increase the field of view of the camera fixed to the distal tip because of the bent section near the distal end of the cannula. When the endoscope is rotated, the display module can be moved relative to the handle 140 in order to maintain the display in a relatively stationary position, or other ergonomic position.

Figure 15A:
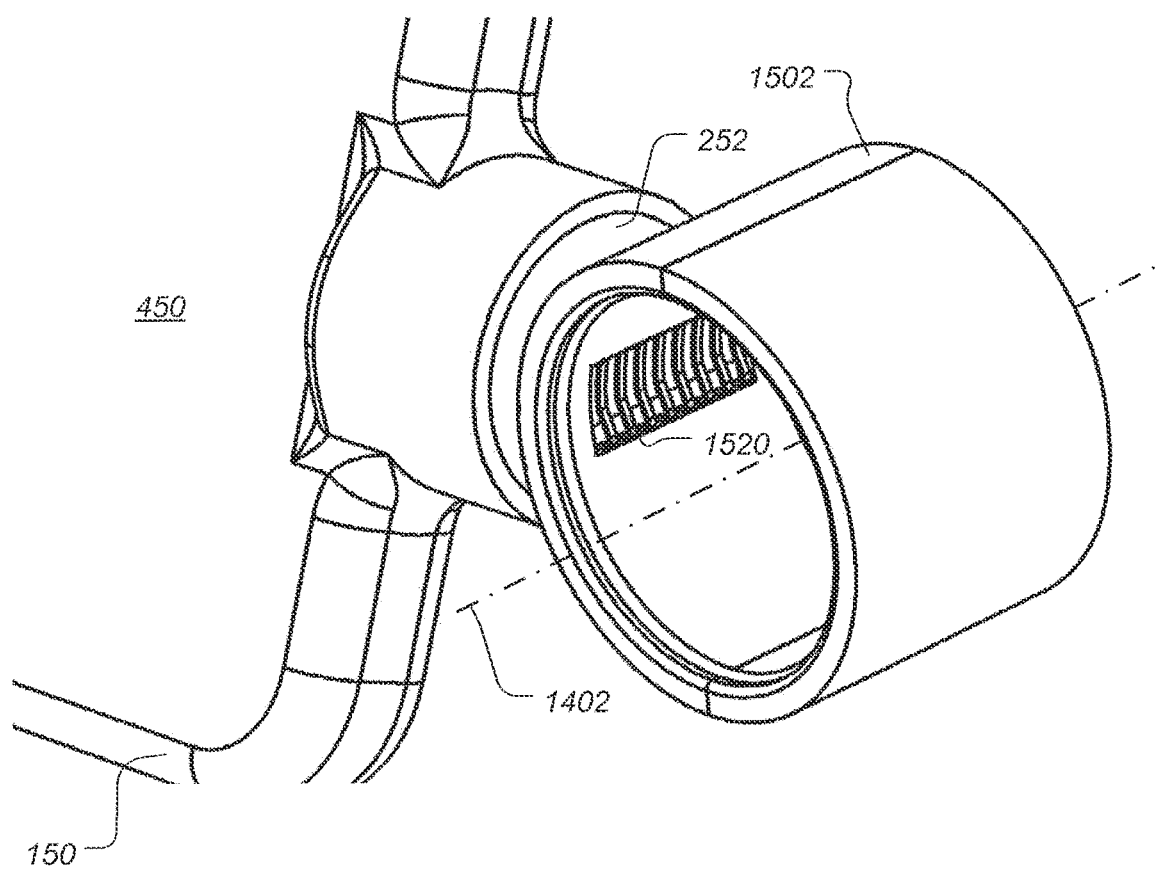
FIGS. 15A-15C are perspective views illustrating various aspects of a handheld surgical endoscope shown in FIG. 14.
Figure 15B:
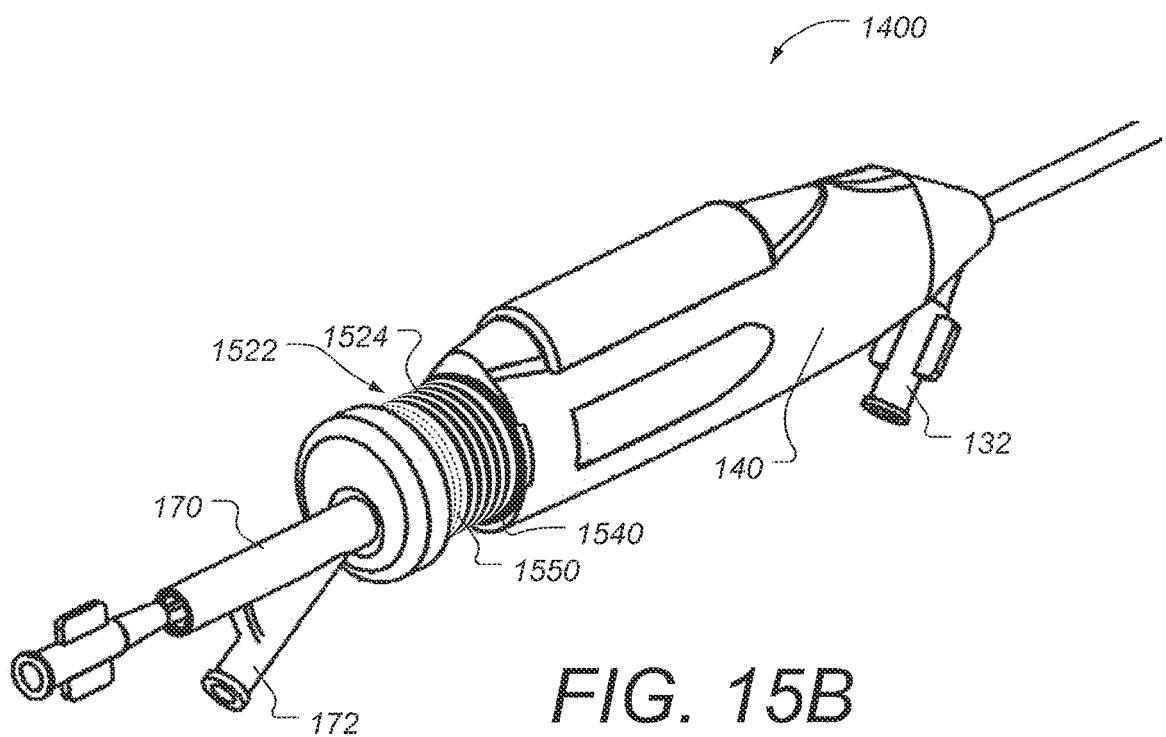
Figure 15C:
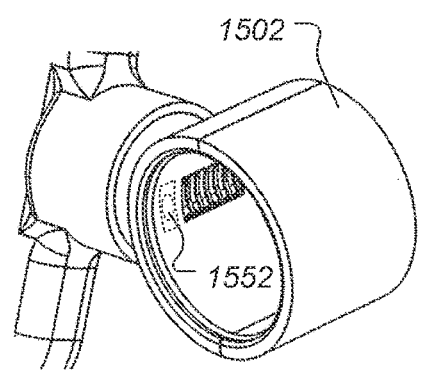

FIGS. 15A-15C are perspective views illustrating various aspects of a handheld surgical endoscope shown in FIG. 14. In FIG. 15A, ring 1502 is visible which wraps around spindle 1522 shown in FIG. 15B. The ring 1502 has a plurality of pins 1520 on its inner surface that make electrical contact with the plurality of contact rings 1524 on spindle 1522. O-rings are provided on either side of the electrical contact of which o-ring 1540 is visible in FIG. 15B.

Note that in cases where display module 150 is fixed to the handle (i.e. not rotatable about the main axis of the endoscope, as in endoscope 100 shown in FIGS. 1-5), the video display is always in a fixed alignment with the camera module at the tip. However in cases where display module 150 is rotatable about the main axis 1402 of the endoscope (such as with endoscope 1400 shown in FIGS. 14 and 15A-15C), the display can be out of alignment with the camera module. When the endoscope 1400 is rotatable during a surgical procedure it is therefore useful to have some feedback to the user as to the rotational position of the bent portion of the tip. In such cases the fluid ports 132 and 172 can serve as an tactile feedback to aid user. According to some embodiments, in cases where display module 150 is rotatable about the main axis 1402 of the endoscope (such as with endoscope 1400 shown in FIGS. 14 and 15A-15C), an optical sensor 1552, shown in FIG. 15C, can be used to sense the rotational position of the display module 150 with respect to the handle 140 by reading an encoded pattern 1550 on the outer surface of spindle 1524. The rotational position of the display module 150 relative to the handle 140 (and therefore also to the camera module) can be used to automatically maintain alignment between the video image being displayed on display 450 and the camera module. According to some other embodiments, the rotational position information can instead be used to display a visual marker to the user on display 450 to provide further feedback.

Figure 16:
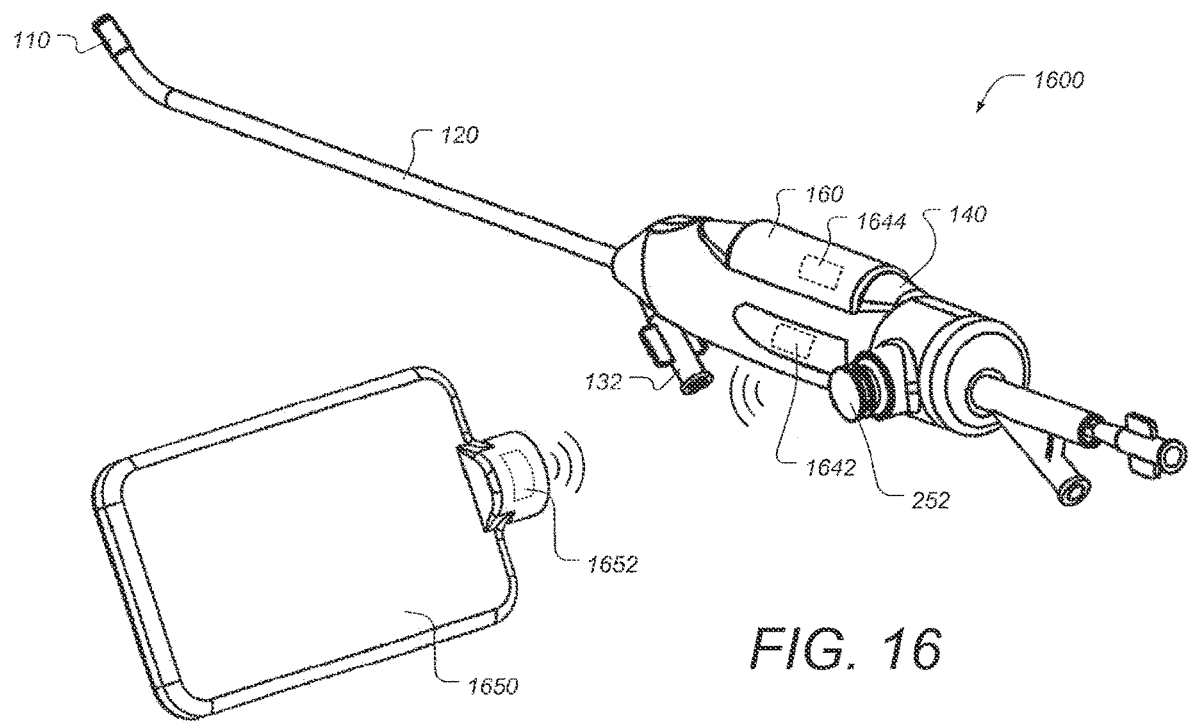
FIG. 16 is a perspective view of a handheld surgical endoscope, according to some embodiments.

FIG. 16 is a perspective view of a handheld surgical endoscope, according to some embodiments. In FIG. 16 the endoscope 1600 has a removable and re-usable display module 1650, just as in the case of display module 150 in endoscopes 100 and 1400 shown in FIGS. 1-5 and 14-15C, respectively. However, in the case of endoscope 1600, the display module 1650 and the handle 140 can communicate with each other via wi-fi or other wireless connection technology. In order to minimize the single-use portion of the endoscope 1600, sensor data from the camera module is transmitted via wireless transmission module 1642 in the handle 140 to the wireless transmission module 1652 on the display module 1650. Complex video functions such as video compression and recording can be carried out by the display module 1650. Some control processing is also carried out by the handle 140 but little or no user interface functionality need to be included in handle 140. For example user interface controls for video on/off, record, lighting, and exposure controls can all be provided via a touch screen graphical user interface on display module 1650. According to some embodiments, the wireless transmission module can alternatively be positioned in battery module 160 as shown by transmission module 1644. Positioning the transmission module 1644 in the re-usable battery module 160 instead of on the single use handle 140 further decreases the cost and complexity of the single use portion of endoscope 1600.

Figure 17:
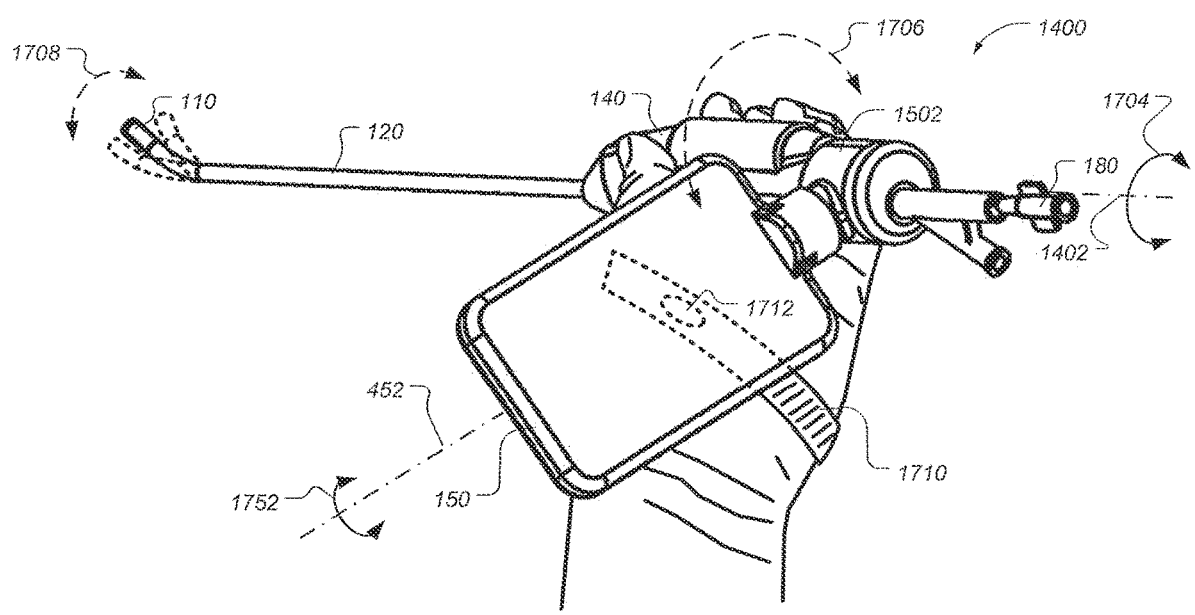
FIG. 17 is a perspective view of a handheld surgical endoscope shown in FIG. 14 configured for one-handed operation, according to some embodiments.

FIG. 17 is a perspective view of a handheld surgical endoscope configured for typically one-handed operation, according to some embodiments. The endoscope 1400 has a display module 150 that is rotatable relative to the handle 140 about a main handle axis 1402 such as shown by arrow 1704. In addition, however, the display module 150 has a strap 1710 attached via mounting 1712 which is dimensioned to wrap around the hand or wrist of a user as shown in FIG. 17. By attaching the display module 150 to the hand or wrist, the user can easily use one hand to rotate the handle cannula and tip of the endoscope 1400, as shown by the dashed arrows 1706 and 1708, while maintaining the display module 150 in a fixed or relatively fixed position for easy viewing. In particular, the strap 1710 effectively prevents display module 150 from rotating about axis 1402 despite the handle 140 and cannula 120 being rotated about the main longitudinal axis of cannula 120. Note that the longitudinal axis of cannula 120 and longitudinal axis of the handle 140 (axis 1402) will be parallel to each other but not necessarily the same depending on the design of the handle 140. Furthermore, by positioning the mounting 1712 near the axis 452, the display module 150 can still be rotated about that axis, which is perpendicular to the cannula axis 1402, as shown by arrow 1752. Allowing for one-handed operation frees up the user's other hand for other tasks such as manipulating a surgical implement such as surgical device 180 shown in FIG. 17 entering the working channel via opening 170. Although the display is shown in FIG. 17 as being attached to a user's left hand, the same or similar strap or fixing mechanism can be used to attach the display to the user's right hand. According to some embodiments, other techniques can be used to attach the display module 150 to the wrist or hand of the user, including bands and/or elastic loops which can be attached via snaps or Velcro, and open or closed ended clips.

Figure 18:
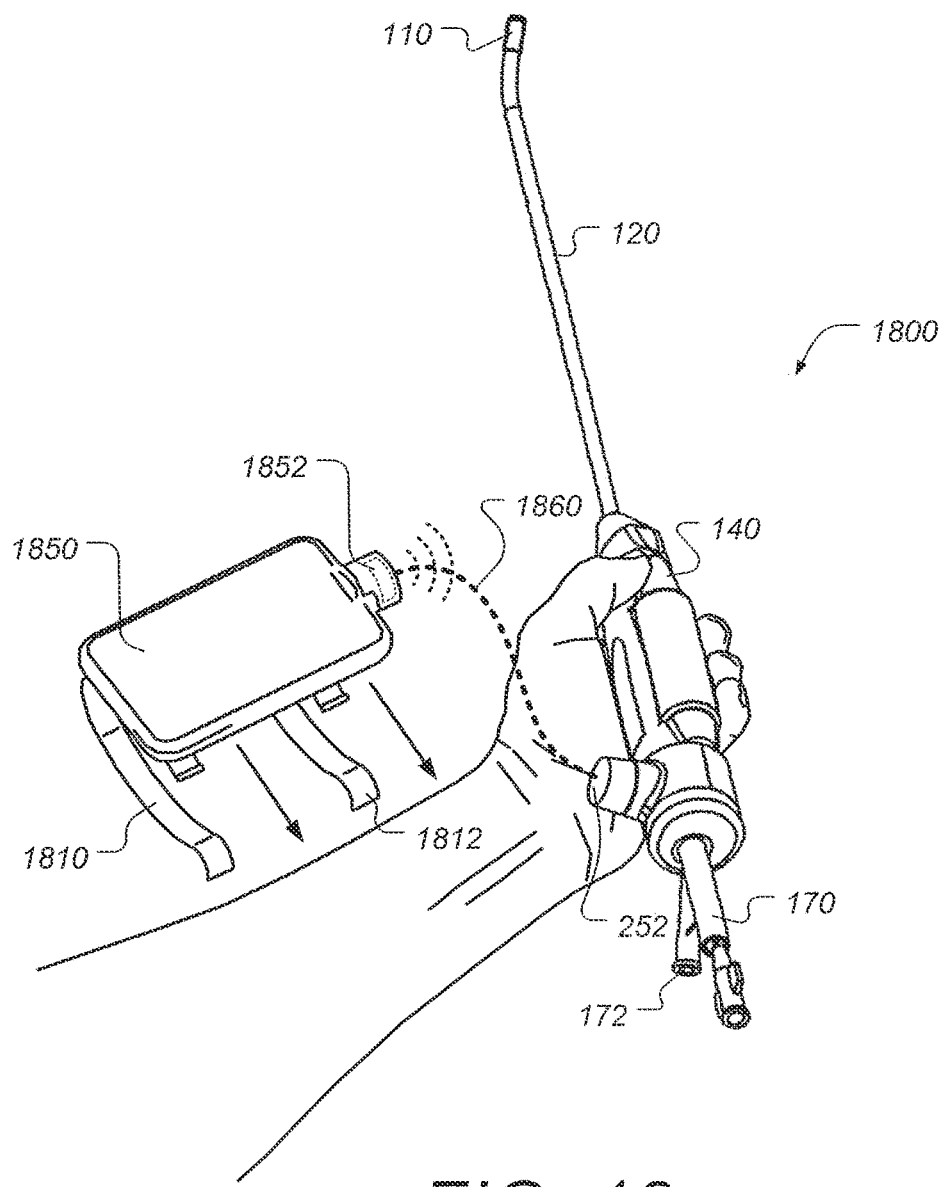
FIG. 18 is a perspective view of a handheld surgical endoscope configured for one-handed operation, according to some other embodiments.

FIG. 18 is a perspective view of a handheld surgical endoscope configured for typically one-handed operation, according to some other embodiments. In FIG. 18 the endoscope 1800 has a removable and re-usable display module 1850 that communicates with the handle 140 while not attached to the handle 140 either using a wireless communication unit 1852 or a flexible cable 1860. If wireless communication is used then this unit can be similar or identical to endoscope 1600 shown in FIG. 16. The display module 1850 has two metal clips 1810 and 1812 that are dimensioned and shaped to attach to the user's forearm as shown in FIG. 18. When attached to the user's forearm, the endoscope 1800 allows for one-handed operation of the endoscope similar to as described with respect to FIG. 17, including the ability to rotate the handle, cannula and tip about the main longitudinal axis, while maintaining the display in a fixed or relatively fixed orientation. As in the case of FIG. 17, the display module can be attached to the user's right or left arm (although attachment to the left forearm is shown in FIG. 18). Furthermore, other techniques can be used to attach the display module 150 to the user's left or right forearm, including, for example, clips otherwise similar to clips 1810 and 1812 but made of a non-metallic material, straps, bands, and/or elastic loops which can be attached via snaps or Velcro.

Figure 19A:
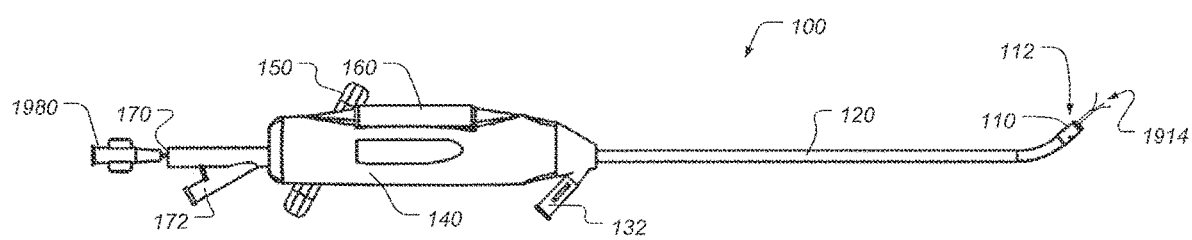
FIGS. 19A and 19B are a right side view and a perspective view, respectively, of a handheld surgical endoscope having an integrated grasping tool, according to some embodiments.
Figure 19B:
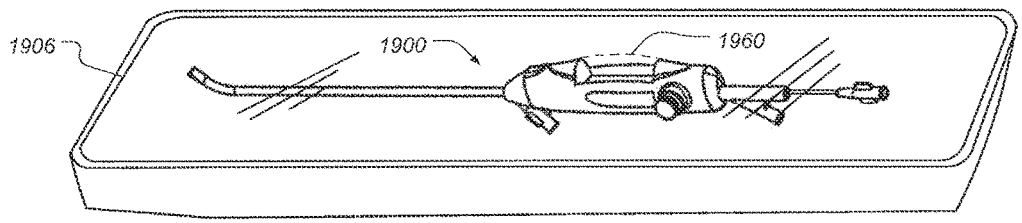
Figure 21A:
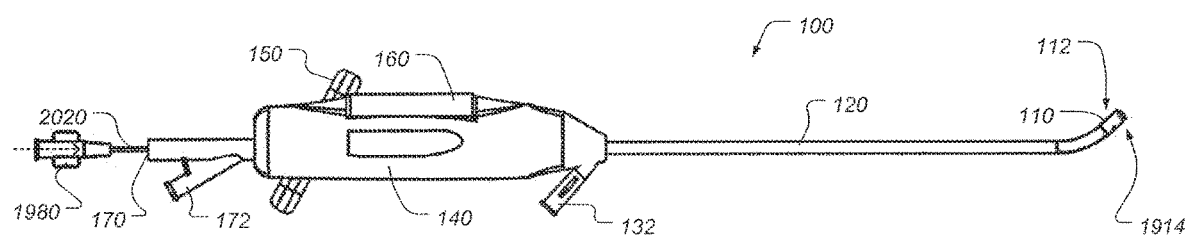
FIGS. 21A and 21B are perspective views showing aspects of grasper actuation for a handheld surgical endoscope according to some embodiments.
Figure 21B:
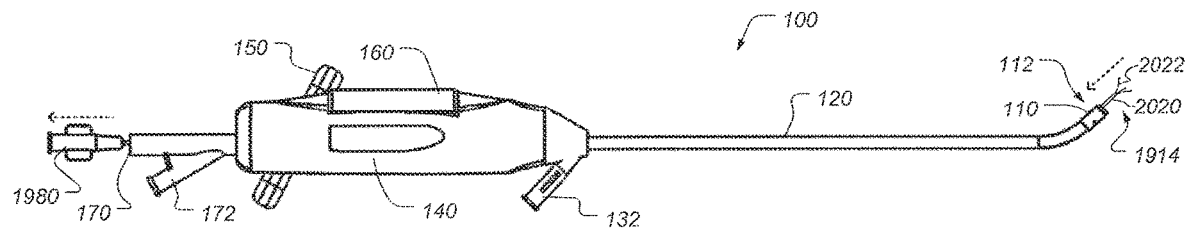

FIGS. 19A and 19B are a right side view and a perspective view, respectively, of a handheld surgical endoscope having an integrated grasping tool, according to some embodiments. The integrated grasping tool can be an example of the surgical device 180 shown in FIG. 1. The surgical endoscope 100 includes an elongated cannula 120 with a distal tip 112 for inserting into a hollow organ or cavity of the body. A grasper 1914 passes through a lumen in cannula 120, such as the working channel indicated by dashed lines 520 in FIG. 5 and/or in lumen 720 as shown in FIGS. 7, 11A-B, 12A-D and/or 13. The grasper 1914 can be extended to protrude distally from distal tip 112 as shown in FIG. 19A by pushing tab 1980 in the distal direction into working channel port 170. The grasper 1914 can be attached to or formed as an integral part of a solid or hollow tube 2020 inserted in the working channel as shown in FIGS. 20B, 21A and 21B. In cases where grasper 1914 includes a hollow tube, it can be made in fluid communication with a fluid line (not shown), which in turn is connected to syringe or other fluid dispensing device (also not shown). The grasper 1914 can be used to obtain a sample of, for example, tissue, cells and/or fluids from an internal wall of an organ.

According to some embodiments, a separate tip sub-assembly 110 is attached to the cannula 120 which can be made from an extruded material. For further details relating to a separate tip sub-assembly for a handheld endoscope, see U.S. patent application Ser. No. 15/371,858 filed Dec. 7, 2016 issued as U.S. Pat. No. 9,895,048 (hereinafter referred to as "the '048 patent"); U.S. Ser. No. 15/462,331 filed Mar. 17, 2017 published as U.S. 2017-0188793 A1 (hereinafter the '331 application); and Int'l. Pat. App. No. PCT/US18/14880 filed Jan. 23, 2018 published as Intl. Pub. No. WO/2018/136950 (hereinafter referred to as "the '880 application"), each of which is hereby incorporated by reference herein.

According to some embodiments, single-use portion 1900, shown in FIG. 19B, is made at a relatively low-cost and is intended to be disposed of after a single-use. By making the tip, cannula, handle and grasper tool all single-use, stringent decontamination and disinfection procedures as well as the risk of cross-contamination and hospital acquired diseases can be significantly lessened or avoided. According to some embodiments the disposable, single-use portion 1900 includes the grasper tool 1914 pre-installed within cannula 120 in a retracted position (as shown in FIGS. 20A and 21A). The single use portion 1900 with grasper pre-installed, is sterilized, for example, during production and is provided to the user in a sealed sterilized pouch 1906, for ease of storage and handling as shown in FIG. 19B. According to some embodiments, battery 160 can be a rechargeable or non rechargeable battery and may be included as part of the single-use disposable portion 1900 (as indicated by dashed line 1960 in FIG. 19B) or it may be detachable and not included in portion 1900. According to some embodiments, as discussed supra, a rechargeable battery may be included within the display module 150 and therefore a separate battery 160 does not need to be mountable to the handle portion 140.

FIGS. 20A and 20B are side and perspective views of the distal tip and show aspects of the grasper actuation, according to some embodiments. FIG. 20A shows tip 112 when the grasper 1914 in the retracted position while FIG. 20B shows tip 112 when the grasper 1914 is in the extended position. Note that while in the retracted position, the claws of the grasper 1914 are fully recessed in working channel port 630 such that the distal-most portion of the grasper 1914 is recessed proximally of the distal opening of port 630 of tip assembly 110. As such, there is no risk of a sharps injury from the tip of grasper 1914.

FIGS. 21A and 21B are perspective views showing aspects of grasper actuation for a handheld surgical endoscope, according to some embodiments. FIG. 21A shows the grasper 1914 is in the retracted position as shown in FIG. 20A, while FIG. 21B shows the grasper 1914 in the extended position as shown in FIG. 20B. Tab 1980 is used to move grasper 1914 relative to the handle 140, cannula 120 and tip 112.

Figure 22C:
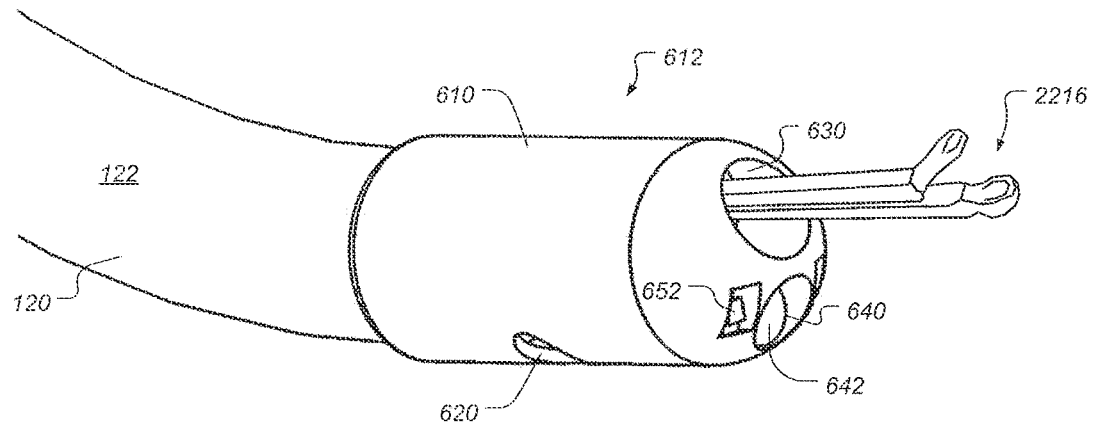

FIGS. 22A, 22B and 22C show a biopsy tool being used in combination with a handheld surgical endoscope, according to some embodiments. FIG. 22A is a side view of the endoscope 100 that in this case includes biopsy forceps 2214 which passes through a lumen in cannula 120, such as the working channel indicated by dashed lines 520 in FIG. 5 and/or in lumen 720 as shown in FIGS. 7, 11A-B, 12A-D and/or 13. The forceps can be an example of the surgical device 180 shown in FIG. 1. The forceps 2214 can be extended to protrude distally from distal tip 112 as shown in FIG. 22A by pushing handle 2280 in the distal direction into working channel port 170. The forceps 2214 can pre-inserted in the working channel as shown in FIG. 22B, and the single use portion with forceps pre-installed, may be sterilized, for example, during production and provided to the user in a sealed sterilized pouch, such as shown in FIG. 19B. Fluid syringe 2270 can also be used to supply fluid through fluid line 2272, for example via proximal fluid port 172 which may be in communication with the working channel 720, such as shown in FIG. 13. According to other embodiments, instead of a syringe, another fluid dispensing device (not shown) can be used. FIG. 22B is a perspective view of the distal tip and shows further detail of the forceps 2214 including a shaft 2220. FIG. 22C shows an alternative type of forceps 2216 that have smoother scoop-like jaws then the forceps 2214.

Figure 23A:
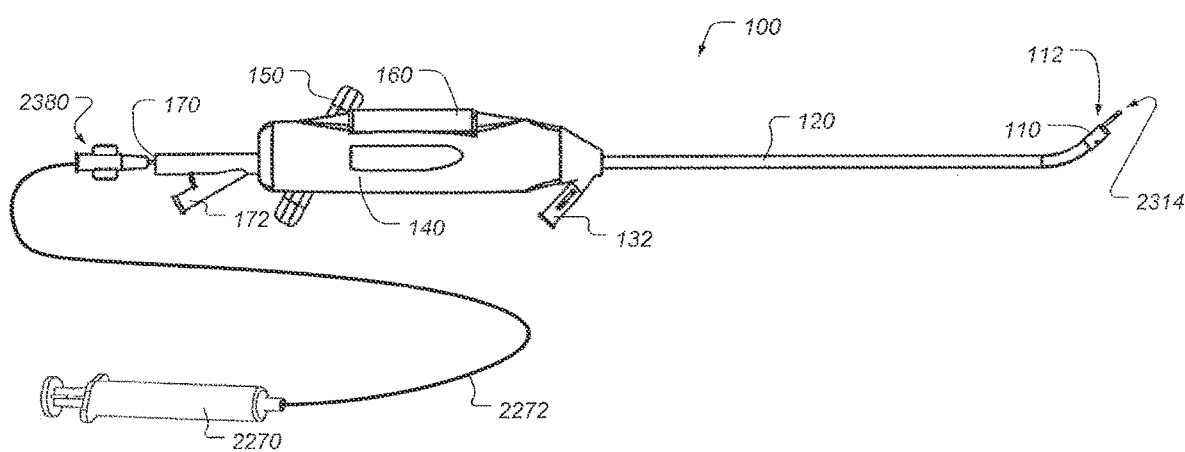
Figure 23D:
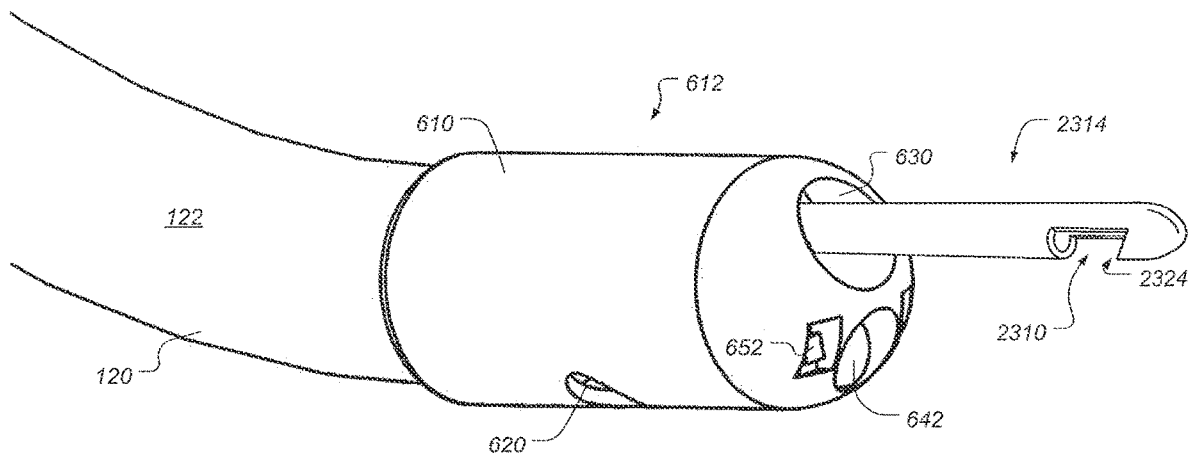

FIGS. 23A, 23B, 23C and 23D show a biopsy tool being used in combination with a handheld surgical endoscope, according to some other embodiments. The biopsy tool can be an example of the surgical device 180 shown in FIG. 1. In this case, the biopsy tool 2314 is formed from a hollow tube that has a notch 2310 formed at its distal end that is configured for cutting the target tissue. As shown in FIG. 23A the syringe 2270 and tube 2272 can be used to supply fluid directly through the hollow tube of biopsy tool 2314 via an opening in tab 2380. According to some embodiments, the tool 2314 can pre-inserted in the working channel. The single use portion with biopsy tool pre-installed, may be sterilized, for example, during production and provided to the user in a sealed sterilized pouch, such as shown in FIG. 19B. FIG. 23B is a perspective view of the distal tip and shows further detail of the biopsy tool 2314. The tip is rounded and there is a notch 2310 cut in one side of the tool as shown. The distal end of the notch 2310 includes a sharp cutting portion 2324. FIG. 23C shows an alternative design in which both the proximal edge 2326 of the notch 2310 is configured for cutting as well as the distal edge 2324. FIG. 23D shows biopsy tool 2314 with the distal notch 2310 facing downwards, towards imaging module 642, which may allow for increased ergonomics and visual feedback to the operator while carrying out the intended procedure. According to some embodiments, the scoop of forceps 2216, the claws of forceps 2214 are also oriented to increase ergonomics and enhance visualization. According to some embodiments, the inserted tool can be re-oriented, such as shown in FIG. 23D, and according to other embodiments, the distal tip can be re-arranged for example such that the imaging module 642 is located above the working channel distal port 630.

The surgical device or tool 180 can comprise an injection needle threaded through the working channel indicated by dashed lines 520 in FIG. 5 and/or in lumen 720 as shown in FIGS. 7, 11A-B, 12A-D and/or 13 to inject medication into tissue or to extract a biological sample, or a pipelle made of a biologically compatible metal or plastic to extract biological samples.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What is claimed is:

1. An endoscope comprising:
    a handle extending along a straight longitudinal axis and having an opening at a proximal end thereof and a cannula permanently secured to said handle and extending distally therefrom along said straight longitudinal axis, said cannula having a distal port at a distal end thereof and a curving distal tip with an imaging module providing images;
    a display unit removably mounted on said handle and comprising a touch-sensitive display screen;
    wherein:
        said display unit and said handle include respective mechanical connectors that engage each other to removably mount the display unit on the handle by sliding motion relative to each other;
        said display unit is mounted on a longitudinal side of the handle such that said display screen thereof in its entirety extends radially away from the handle;
        said display unit and said handle further include respective electrical connectors in the form of female connector hole in one of the display unit and the handle and in the form of male connector pins in the other of the display unit and the handle, wherein said male connector pins directly engage said female connector holes and make electrical contact therewith absent intermediate conduits or cables when the display unit is mounted on said handle;
        said display unit includes a battery powering said screen and said imaging module;
        said cannula includes a working channel extending from said opening at the proximal end of the handle to said distal port at the distal end of the cannula;
        said working channel is configured to extend from said opening at the proximal end of the handle through the handle, and into said cannula along said straight longitudinal axis for insertion and removal of a surgical implement in a patient procedure and is continuous and same size inside all the way from immediately adjacent said opening at the proximal end of the handle to said distal port; and
        said touch-sensitive screen is configured to respond to touch commands to control said imaging module and is further configured to display said images; and
    whereby said display unit is being removable tool-free from said handle for disposal of the handle and cannula after a medical procedure therewith and for tool-free mounting on a new handle for another medical procedure; and
    a surgical device in said working channel, said surgical device comprising a grasper tool configured to move in said working channel between extended positions in which the tool protrudes distally from the distal tip of the cannula and a retracted position in which the tool is recessed in the working channel of the cannula.

2. The endoscope of claim 1, in which said cannula and said display unit are configured for rotation relative to each other about said longitudinal axis.

3. The endoscope of claim 1, in which the cannula further includes a proximal port and a fluid channel communicating with the proximal fluid port and extending distally into said cannula.

4. An endoscope comprising:
    a handle extending along a longitudinal axis and having an opening at a proximal end thereof and a cannula permanently secured to said handle and extending distally therefrom along said longitudinal axis, said cannula having a distal port at a distal end thereof and a distal tip with an imaging module providing images;
    a display unit removably mounted on said handle and comprising a touch-sensitive display screen;
    wherein:
        said display unit is mounted on a longitudinal side of the handle such that all of said display screen thereof extends radially away from the handle;
        said cannula includes a working channel extending from said opening at the proximal end of the handle to said distal port at the distal end of the cannula;
        said working channel is configured to extend from said opening at the proximal end of the handle through the handle, into said cannula and to a distal region of the cannula along said longitudinal axis for insertion and removal of a surgical implement in a patient procedure and is continuous and integral and the same size inside all the way from immediately adjacent said opening at the proximal end of the handle to said distal port; and
        said touch-sensitive screen is configured to respond to touch commands to control said imaging module and is further configured to display said images;
    whereby said display unit is removable tool-free from said handle for disposal of the handle and cannula after a medical procedure therewith and for tool-free mounting on a new handle for another medical procedure; and
    a surgical device in said working channel, said surgical device comprising a tool configured to move in said working channel between extended positions in which the tool protrudes distally from the distal tip of the cannula and a retracted position in which the tool is recessed in the working channel of the cannula.

5. The endoscope of claim 4, in which said cannula and said display unit are configured for rotation relative to each other about said longitudinal axis.

6. An endoscope comprising:
    a handle extending along a longitudinal axis and having an opening at a proximal end thereof and a cannula permanently secured to said handle and extending distally therefrom along said longitudinal axis, said cannula having a distal port at a distal end thereof and a distal tip with an imaging module providing images;
    a display unit removably mounted on said handle and comprising a touch-sensitive display screen;
    wherein:
        said display unit is mounted on a longitudinal side of the handle such that all of said display screen thereof extends radially away from the handle;
        said cannula includes a working channel extending from said opening at the proximal end of the handle to said distal port at the distal end of the cannula;

said working channel is configured to extend from said opening at the proximal end of the handle through the handle, into said cannula, and to said distal port along said longitudinal axis for insertion and removal of a surgical implement in a patient procedure and is continuous and integral and the same size inside all the way from immediately adjacent said opening to said distal port; and said touch-sensitive screen is configured to respond to touch commands to control said imaging module and is further configured to display said images;

whereby said display unit is removable tool-free from said handle for disposal of the handle and cannula after a medical procedure therewith and for tool-free mounting on a new handle for another medical procedure; and a surgical device in said working channel, said surgical device comprising a tubular biopsy tool configured to take a biological sample from the patient's body, said tubular biopsy tool configured to move in said working channel between extended positions in which the tool protrudes distally from the distal tip of the cannula and a retracted position in which the tool is recessed in the working channel of the cannula.

7. The endoscope of claim 6, in which said cannula and said display unit are configured for rotation relative to each other about said longitudinal axis.

\* \* \* \* \*